United States Patent [19]

Naito et al.

[11] Patent Number: 4,980,464
[45] Date of Patent: Dec. 25, 1990

[54] METHOD FOR PRODUCTION OF CEPHALOSPORIN COMPOUNDS

[75] Inventors: Kenzo Naito, Kyoto; Yukio Ishibashi, Osaka, both of Japan

[73] Assignee: Takeda Chemical Industries, Ltd., Osaka, Japan

[21] Appl. No.: 373,594

[22] Filed: Jun. 30, 1989

Related U.S. Application Data

[63] Continuation of Ser. No. 16,763, Feb. 19, 1987, abandoned.

[30] Foreign Application Priority Data

Feb. 28, 1986 [JP] Japan .................................. 61-44992

[51] Int. Cl.$^5$ .......................................... C07D 501/04
[52] U.S. Cl. .................................. 540/222; 540/221; 540/225; 540/226; 540/227; 540/228; 540/230
[58] Field of Search ............... 540/227, 221, 222, 226, 540/225, 230

[56] References Cited

U.S. PATENT DOCUMENTS 4,801,703 1/1989 Natter et al. .................. 540/227
4,902,793 2/1990 Nishikido et al. .............. 540/222

FOREIGN PATENT DOCUMENTS 1511195A 7/1986 Japan .
2108114 9/1982 United Kingdom .
2147900 9/1982 United Kingdom .

OTHER PUBLICATIONS

Chemical Abstracts, vol. 106, No. 3 (1987), p. 576, No. 18246b.

Primary Examiner—Nicholas S. Rizzo
Attorney, Agent, or Firm—Wegner, Cantor, Mueller & Player

[57] ABSTRACT

A method for producing a compound of the formula;

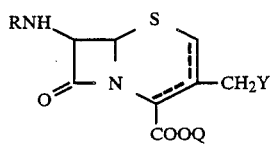

wherein R stands for a hydrogen atom, an acyl group or a protective group other than acyl groups, Q stands for a hydrogen atom or an ester residue, Y stands for the residue of a nucleophilic compound and the dotted line shows the double bond at 2- or 3- position of the cephem ring or a salt thereof, characterized by allowing a compound of the formula;

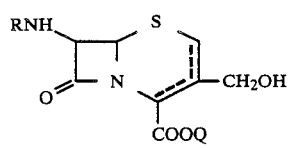

[R, Q and the dotted line are of the same meaning as above] or a salt thereof to react with a nucleophilic compound or a salt thereof and a compound of the formula;

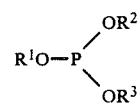

wherein $R^1$, $R^2$, $R^3$ independently stand for a hydrocarbon group having not more than 8 carbon atoms, or $R^1$ and $R^2$, $R^1$ and $R^3$ or $R^2$ and $R^3$ may be combined to form polymethylene group, according to which the end product [I] of high quality can be provided in a high yield by one reaction step by using the compound [III] of relatively low cost, thus the method of this invention is advantageous for mass-producing the compound [I] on an industrial scale from the compound [II] and a nucleophilic compound.

7 Claims, No Drawings

METHOD FOR PRODUCTION OF CEPHALOSPORIN COMPOUNDS

This application is a continuation of Ser. No. 016,763, filed Feb. 19, 1987, now abandoned.

This invention relates to an industrially advantageous method for producing a compound of the formula

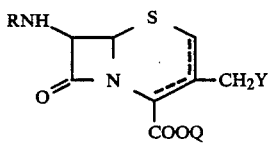

wherein R stands for hydrogen atom, an acyl group or a protective group other than acyl groups, Q stands for hydrogen atom or an ester residue, Y stands for the residue of a nucleophilic compound, and the dotted line shows the double bond at the 2- or 3-position (the compound [I] should be construed as including also a salt thereof and the same shall apply hereinafter), by using as starting materials a compound of the formula

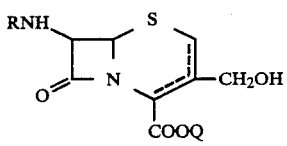

wherein R, Q and the dotted line are of the same meaning as defined above (the compound [II] should be construed as including also a salt thereof and the same shall apply hereinafter), and a nucleophilic compound or a salt thereof.

The compound [I] is important as an antibacterial compound or an intermediate for synthesizing antibacterial compounds, and methods of preparing the compound [I] have been studied and researched extensively. Industrially employable starting materials of cephem compounds are principally cephalosporin C (CPC) producible fermentatively or a 3-acetoxymethyl cephem compound derived therefrom and deacetyl cephalosporin C (DCPC) or 3-hydroxymethyl cephem compound [II] producible by subjecting DCPC or CPC to chemical or enzymatic reaction. Heretofore compounds of [I] have been produced by substituting their acetoxy group or hydroxy group of them with a nucleophilic compound. However, for substituting a nucleophilic group for the acetoxy group of a 3-acetoxymethyl cephem compound, due to relatively low reactivity of acetoxy group, heating or use of a large amount of an acid catalyst is required, and, therefore, lowering of the yield due to decomposition of the cephalosporin under such conditions as above is unavoidable and use of a large amount of strong acid requires some restrictions on industrial equipment or requires complicate after-treatment. On the other hand, methods which comprise substitution of a more reactive group for the hydroxy group of 3-hydroxymethyl cephem compound [II] followed by allowing the resultant compound to react with a nucleophilic compound have been studied. These methods are exemplified by:

(1) a method which comprises substituting a halogeno group for the hydroxy group at the 3-position followed by allowing the resultant product to react with a nucleophilic substance (e.g. Belgian patent No. 719,710), (2) a method which comprises substituting a more reactive acyloxy group (e.g. acetoacetoxy group) compared with acetoxy group for the hydroxy group at 3-position followed by allowing the resultant product to react with a nucleophilic substance (e.g. British Patent No. 1544103), and (3) a method which comprises allowing a compound [II] to react with a nucleophilic compound and a cyclic phosphorus compound having the partial structure representable by the formula;

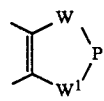

[wherein W, $w^1$ stand for O, S, NH or a hydrocarbon-substituted amino group] in an organic solvent (e.g. British Patents Nos. 2108114 and 2147900).

In both methods (1) and (2), however, two reaction processes are required to be conducted separately resulting in increase of reaction steps in number and requiring a great deal of labour while lowering the overall yield. Besides, in the method (1), a side reaction forming a lactone ring with the carboxyl group at the 4-position and the hydroxyl group at the 3-position during the halogenation of the hydroxyl group occurs easily, and, for preventing this, protection of the carboxyl group at 4-position by its esterification, for example, is essential. This esterification should naturally be followed by de-esterification, which makes the process more complicate. In the method (2), depending on the kinds of acyloxy group of 3-acyloxymethyl, better reactivity can be expected, but not sufficient, and, depending on the acylating agent employed, lactone ring formation is apt to occur as the side reaction resulting in lowering the yield. In the method (3), cyclic phosphorus compounds employed, which contain a double bond in the ring, are unstable against the moisture in the air and are easily hydrolized. Besides, the cyclic phosphorus compounds are relatively expensive, thus being less advantageous for mass production on an industrial scale.

No fully satisfactory method for commercial production of the end product [I] employing a compound [II] and a nucleophilic compound has been found yet, and, in view of the great demand for the end product [I], an advantageous method has been desired.

Circumstances being such as mentioned in the foregoing, the present inventors have conducted extensive studies on various methods of preparing the cephalosporin compound [I], resulting in finding that a compound [I] of high quality can be unexpectedly prepared in a high yield by a single step which comprises allowing a compound [II] obtained by subjecting DCPC or CPC producible in a high potency by fermentative cultivation to chemical or enzymatic reaction to react with a nucleophilic compound and a compound of the formula

[wherein $R^1$, $R^2$ and $R^3$ each stand for a hydrocarbon group having not more than 8 carbon atoms, and $R^1$ and $R^2$, $R^1$ and $R^3$ or $R^2$ and $R^3$ may be combined to form a polymethylene group] which has never been used in the field of production of [II] from [I] and that, as the compound [III] is less expensive, the end product [I] can be prepared in a large amount on an industrial scale. Furthermore, it was also found that the process with use of the compound [III] has the following advantageous features from the view-point of industrial application.

(1) the compound [III] is more stable particularly as compared with the cyclic phosphorus compound used in the known method (3) mentioned above, which facilitates the employment and handling of the compound [III].

(2) the ester-linkage of the phosphorous compound [III] is hydrolized, with the reaction proceeding, to produce corresponding alcohols as by-product, which are easily removed from the desired compound by e.g. distillation;

(3) the compound [III] acts as a reducing agent and thus is capable of preventing the coloring of the product compound [I] due to oxidation;

(4) the reaction with use of the compound [III] is mild and not exothermic, which enables the reaction very efficiently to be carried out at room temperature without heating and cooling. The present invention was completed on the basis of this finding.

The present invention therefore relates to a method of preparing the compound [I], which is characterised by allowing a compound [II] to react with a nucleophilic compound and a compound [III].

In the above formulae, R stands for hydrogen atom, an acyl group or a protecting group other than acyl groups. The acyl group is well known in the β-lactam antibiotic field and exemplified by known ones such as the acyl group substituted at the amino group at the 6-position of a penicillin derivative or the acyl group substituted at the amino group at the 7-position of a cephalosporin derivative. Specific examples of these acyl groups include those led by eliminating OH from carboxylic acid, which are further exemplified by groups representable by the formula $R_a$—CO— [IV] [wherein $R^a$ stands for hydrogen atom, alkyl*, phenyl* or heterocyclic* group], groups representable by the formula

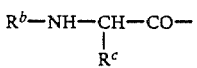

[wherein $R^b$ stands for hydrogen, amino acid residue, a protective group of amino group or a group representable by the formula $R^d$—(CH$_2$)n$_1$—CO— { wherein $R^d$ stands for a heterocyclic* group and n$_1$ denotes an integer of 0 to 2}, and $R^c$ stands for alkyl, phenyl* and a heterocyclic* group], groups representable by the formula $R^3$—$R^f$—CO— [VI] [wherein $R^e$ stands for a group representable by the formula

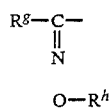

{wherein $R^g$ stands alkyl*, a heterocyclic* group or phenyl* and $R^h$ stands for hydrogen, alkyl* or a group representable by the formula —$R^i$—$R^j$ (wherein $R^i$ stands for alkylene or alkenylene* and $R^j$ stands for phenyl*, carboxyl or an ester or mono- or dialkylamino thereof, respectively), respectively}, and $R^f$ stands for a bond itself or a group representable by the formula

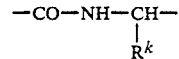

(wherein $R^k$ stands for alkyl, phenyl* or thiazolyl* group), respectively], a group representable by the formula [wherein $R^l$ stands for hydroxy, hydroxysulfonyloxy, carboxy,

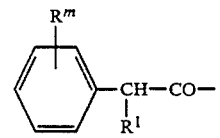

ureido*, sulfamoyl*, sulfo or phenoxy* carbonylformyloxy, and $R^m$ stands for hydrogen, alkyl, alkoxy, halogen, nitro, hydroxy, respectively], and a group representable by the formula $R^n$—$R^o$—CH$_2$—CO— [VIII] [wherein $R^n$ stands for cyano, phenyl*, phenoxy*, acyloxy, alkenyl* or heterocyclic* group, and $R^o$ stands for a bond itself or —S—, respectively], etc. As for the groups represented by the afore-mentioned symbols $R^a$ to $R^o$ as well as groups described throughout this specification, the following definition respectively shall apply with the number of carbon atoms, when particularly specified, varied accordingly, unless otherwise defined. When they are "optionally substituted ones", they are shown by attaching asterisk * on the right shoulder thereof. For instance, "optionally substituted alkyl" is shown by "alkyl*". In this case, the number of the substituents is not limited to one, but, depending on the groups to be substituted, 2 to several number of substitutents, preferably 2 to 8 substitutents, more preferably 2 or 3 substituents, which may be the same or different from one another, may be attached. Preferable alkyl groups are straight-chain or branched lower ones having 1 to 6 carbon atoms, as exemplified by methyl, ethyl, n-propyl, isopropyl, n-butyl, isobutyl, tert-butyl, n-pentyl, isopentyl, n-hexyl, isohexyl, etc. Especially, "lower alkyl group" means such alkyl having 1 to 6 carbon atoms unless otherwise specified. Preferable alkenyl groups are straight-chain or branched lower alkenyl groups having 2 to 6 carbon atoms, as exemplified by vinyl, allyl, isopropenyl, 2-methallyl, 2-butenyl, 3-butenyl, etc. As heterocyclic groups are mentioned 5 to 8 membered ring containing 1 to several (preferably 1 to 4) hetero-atoms selected from among nitrogen atom (optionally oxides thereof), oxygen atom and sulfur atom, or condensed ring thereof, those having a bond itself at the carbon atom, which are exemplified by 2- or 3-pyrrolyl, 2- or 3-furyl, 2- or 3-thienyl, 2- or 3-pyrrolidinyl, 2-, 3- or 4-pyridyl, N-oxido-2-, 3- or 4-pyridyl, 2-, 3- or 4-piperidinyl, 2-, 3or 4-pyranyl, 2-, 3- or 4-thiopyranyl, pyradinyl, 2-, 4- or 5-thiazolyl, 2-, 4- or 5-oxazolyl, 3-, 4- or 5-isothiazolyl, 3-, 4- or 5-isoxazolyl, 2-, 4- or 5-imidazolyl, 3-, 4- or 5-pyrazolyl, 3- or 4-pyridazinyl, N-oxido-3- or 4-pyridazinyl, 2-, 4- or 5-pyrimidinyl, N-oxido-2-, 4- or 5-pyrimidinyl, piperazinyl, 4- or 5-(1,2,3-thiadiazolyl), 3- or 5-(1,3,4-thiadiazolyl), 1,3,4-thiadiazolyl, 1,2,5-thiadiazolyl, 4- or 5-(1,2,3-oxidiazolyl), 3- or 5-(1,2,4-oxadiazolyl), 1,3,4-oxadiazolyl, 1,2,5-oxadiazolyl, 1,2,3- or 1,2,4-triazolyl, 1H or 2H-tetrazolyl, pyrido[2,3-d]pyrimidyl, benzopyranyl, 1,8-, 1,4-, 1,6-, 1,7-, 2,7- or 2,6-naphthylidyl, quinolyl, thieno[2,3-d]pyridyl, imidazo[1,2-a]pyridinium-1-yl, 2,3-cyclopenteno-1-pyridinio, imidazo[1,5-a]pyridinium-2-yl, imidazo[1,2-b]pyridazinium-1-yl, etc., which are subjected to common use. Preferably alkoxy groups are straight-chain or branched lower alkoxy groups having 1 to 6 carbon atoms, which are exemplified by methoxy, ethoxy, n-propoxy, isopropoxy, n-butoxy, isobutoxy, sec-butoxy, tert-butoxy, n-pentyloxy, isopentyloxy, n-hexyloxy, isohexyloxy, etc. As halogen are used fluorine, chlorine, bromine or iodine. As amino acid residue are exemplified glycyl, alanyl, valyl, leucyl, isoleucyl, seryl, threonyl, cysteinyl, cystyl, methionyl, α- or β-asparagyl, α- or γ-glutamyl, lysyl, arginyl, phenylalanyl, phenylglycyl, tyrosyl, histidyl, triptophanyl, prolyl, etc. The aminoacid residues include not only the residues of D-amino acid but also those of L-amino acid. Preferable alkylene is lower alkylene having 1 to 3 carbon atoms, as exemplified by methylene, ethylene, propylene, isopropylene, etc. Preferably alkenylene is straight-chain or branched lower alkenylene having 2 to 4 carbon atoms, as exemplified by vinylene, propenylene, etc. As ester of carboxyl group are used lower alkyl ester having 1 to 6 carbon atoms, as exemplified by methyl ester, ethyl ester, propyl ester, n-butyl ester, isobutyl ester, tert-butyl ester, etc. As amino-protecting groups shown by $R^b$ are conveniently employed those which are used for this purpose in the field of synthesizing β-lactam and peptide. More concretely stating, they are exemplified by aromatic acyl groups such as phthaloyl, toluoyl, naphthoyl, benzoyl, chlorobenzoyl, p-nitrobenzoyl, p-tert-butylbenzoyl, p-tert-butylbenzene-sulfonyl, benzenesulfonyl, toluenesulfonyl, phenylacetyl, etc., aliphatic acyl groups such as formyl, acetyl, propionyl, valeryl, caprylyl, n-decanoyl, acryloyl, pivaloyl, monochloroacetyl, dichloroacetyl, trichloroacetyl, methanesulfonyl, ethanesulfonyl, camphorsulfonyl, trifluoroacetyl, maleyl, succinyl, etc., esterified carboxyl groups such as methoxycarbonyl, ethoxycarbonyl, t-butoxycarbonyl, isopropoxycarbonyl, 2-cyanoethoxycarbonyl, β, β, β-trichloroethoxycarbonyl, β-trimethylsilylethoxycarbonyl, β-methylsulfonylethoxycarbonyl, benzyloxycarbonyl, p-nitrobenzyloxycarbonyl, p-methoxybenzyloxycarbonyl, diphenylmethyloxycarbonyl, methoxymethyloxycarbonyl, acetylmethyloxycarbonyl, isobornyloxycarbonyl, phenyloxycarbonyl, etc., substituted carbamoyl groups such as methylcarbamoyl, phenylcarbamoyl, naphthylcarbamoyl, etc.; further, e.g. trityl, 1-methyl-2-ethoxycarbonylvinyl, 2,2-diethoxycarbonylvinyl, 3-oxobute-1-en-1-yl, 2-nnitrophenylthio, benzylidene, 4-nitrobenzylidene, trialkylsilyl, benzyl, p-nitrobenzyl; phosphoryl groups such as diethylphosphoryl, dimethylphosphoryl, diphenylphosphoryl, di-isopropylphosphoryl, di-isobutylphosphoryl, dibutylphosphoryl, o-hydroxyphenylphosphoryl, methyl(o-hydroxyphenyl)phosphoryl, etc., phosphinyl groups such as diemthylphosphinyl, diphenylphosphinyl, etc., phosphonyl groups such as phenylphosphonyl, butylphosphonyl, etc., which are amino-protecting groups other than acyl groups. From among these protecting groups set forth above, any one can be optionally selected for the purpose of this invention.

Among these optionally substituted groups alkyl, alkenyl and alkenylene may have 1 to 3 substituents such as cycloalkyl*, cycloalkenyl* aryl*, heterocyclic* group, alkoxycarbonyl, acyl, oxo, halogen, cyano, trifluoromethyl, hydroxy, alkoxy, aryl*oxy, acryloxy, carbamoyloxy, hydroxysulfonyloxy, alkylsulfonyloxy, aryl* sulfonyloxy, nitro, amino, carboxyl, aminocarbonyl, alkylthiocarbonyl, mercapto, alkylthio, aminoalkylthio, acylaminoalkylthio, aralykyl*thio, aryl*thio, heterocyclic*thio, quaternary ammonium*, alkenyl* etc.

As substituted alkyl groups are employed those representable by, for example, the formula

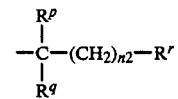

[wherein $n_2$ denotes an integer of 0pg,15 to 3, $R^p$ and $R^q$ independently stand for hydrogen atom, alkyl, cycloalkyl*, aralkyl*, aryl*, heterocyclic* group, alkoxycarbonyl, acyl, or $R^p$ and $R^q$, taken together, stand for oxo, and $R^r$ stands for hydrogen atom, alkyl, cycloalkyl*, cycloalkenyl*, aryl*, heterocyclic* group halogen, cyano, hydroxy, alkoxy, aryl*oxy, acyloxy, carbamoyloxy, hydroxysulfonyloxy, alkylsulfonyloxy, aryl* sulfonyloxy, nitro, amino, carboxy, alkoxycarbonyl, aminocarbonyl, alkylthiocarbonyl, acyl, mercapto, alkylthio, aminoalkylthio, acylaminoalkylthio, aralkyl*thio, aryl*thio, heterocyclic* thio or quaternary ammonium*]. As the cycloalkyl groups are preferable those having 3 to 8 carbon atoms, and use is made of for example cyclopropyl, cyclobutyl, cyclopentyl, cyclohexyl, cycloheptyl, adamantyl, etc. As the aryl groups use is made of, among other, phenyl, α-naphthyl, β-naphthyl, biphenyl and anthryl, especially phenyl and naphthyl etc. being often used. As the aralkyl groups, use is made of, for example, benzyl, phenethyl, phenylpropyl or naphthylmethyl. As the acyl groups, use is made of, for example, formyl, alkylcarbonyl, aryl* carbonyl, aralkyl* carbonyl, heterocyclic* acetyl, especially, for example, acetyl, propionyl, n-butyryl, isobutyryl, n-pentanoyl, n-hexanoyl, benzoyl, 4-hydroxybenzoyl, 4-methoxybenzoyl, phenylacetyl, 4-hydroxyphenylacetyl, 4-methoxyphenylacetyl, 2-thienylcarbonyl, 2-furylcarbonyl, 2-, 4- or 5-thiazolylacetyl, 2- or 3-thienylacetyl, 2- or 3-furylacetyl, 2-amino-4 or t-thiazolylacetyl, etc. As the quarternary ammonium group, use is made of, for example, pyridinium, quinolinium, etc. These quarternary ammonium group may form an intramolecular salt with a counter ion from an acid-radical such as carboxylic group. As the cycloalkenyl group, use is made of, for example, 1-cyclopropenyl, 1-cyclohexenyl, 1-cycloheptenyl, etc. having 3 to 8 carbon atoms.

As the substituents of cycloalkyl*, cycloalkenyl*, aralkyl*, aryl*, heterocyclic* group and quaternary ammonium*, use is made of, for example, alkyl, alkoxy, alkenyl, aryl, aralkyl, mercaptio, alkylthio, arylthio, aralkylthio, alkylsulfonyl, arylsulfonyl, aralkylsulfonyl, hydroxy, oxo, thioxo, halogen, nitro, amino, cyano, carbamoyl, carboxy, acyl, acyloxy, acylamino, hydroxyalkyl, carboxyalkyl, halogenoalkyl, mono- or dialkylaminoalkyl, etc.

As the substituents of pehnoxy*, use is made of such as those of aryl* described in the foregoing. Further, as the substituents of thiazolyl*, use is made of acylamino having 3 to 4 carbon atoms substituted with for example alkyl, alkoxy, halogen, hydroxy, amino, etc. As the substituents of heterocyclic* group, use may be made of phenyl substituted with for example alkyl, alkoxy, halogen, nitro, amino, etc. As the substituents of ureido*, use is made of, for example, sulfo, carbamoyl, sulfamoyl, amidino, alkyl having 1 to 3 carbon atoms, which are in a form of suitable salt with sodium, potassium, etc. As the substituents of sulfamoyl*, use is made of, for example, lower alkyl having 1 to 3 carbon atoms, amidino, etc. As the substituents of alkenylene*, use is made of, for example, carboxy, cyano, etc.

The formula

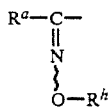

stands for a syn-isomer representable by the formula

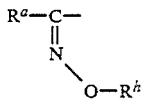

and an anti-isomer representable by the formula

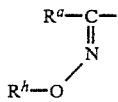

or a mixture thereof.

In the above-mentioned acyl group represented by R, concrete examples of the acyl group representable by the formula $R^a$—CO— are, among others, formyl, acetyl, hexanoyl, benzoyl, p-nitrobenzoyl, 3-(2,6-dichlorophenyl)-5-methylisoxazol-4-yl-carbonyl, 5-methyl-3phenyl-4-isoxazolylcarbonyl, and 4-ethyl-2,3dioxo-1piperazinocarbonyl.

As the practical examples of the acyl group representable by the formula

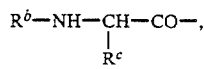

are mentioned D-alanyl, benzyl $N^a$-carbobenzoxy-γ-D-glutamyl-D-alanyl, D-phenylglycyl-D-alanyl, N-carbobenzoxy-D-alanyl, N-carbobenzoxy-D-phenylglycyl, D-alanyl-D-phenylglycyl, γ-D-glutamyl-D-alanyl, 2-(4-ethyl-2,3-dioxo-1-piperazinocarboxamido)-2-phenylacetyl, 2-(4-ethyl-2,3-dioxo-1-piperazinocarboxamido)-2-4-(sulfoxyphenyl)acetyl, N-(4-ethyl-2,3-dioxo-1-piperazinocarbonyl)-D-alanyl, N-(4-ethyl-2,3-dithioxo-1piperazinocarbonyl)-D-phenylglycyl, 2,2-bis-(4-ethyl-2,3-dioxo-1-piperazinocarboxamido)acetyl, 2-(2-amino-4thiazolyl)-2-(4-ethyl-2,3-dioxo-1piperazinocarboxamido)acetyl, 2-(4-hydroxy-6-methylnicotinamido)-2-phenylacetyl, 2-(4-hydroxy-6-methylnicotinamido)-2-(4-hydroxyphenyl)acetyl, 2-{5,8-dihydro-2-(4formyl-1-piperazinyl)-5-oxopyrido[2,3-d]pyrimidine-6 -carboxamido}-2-phenylacetyl, 2-(3,5-dioxo-1,2,4-triazine-6-carboxamido)-2-(4-hydroxyphenyl)acetyl, 2(3-furfurylideneamino-2-oxoimidazolidine-1-carboxamido)-2-phenylacetyl, 2-(coumarin-3-carboxamido)-2-phenylacetyl, 2-(4-hydroxy-7-methyl-1,8-naphthyridine-3-carboxamido)-2-phenylacetyl, 2-(4-hydroxy-7-trifluoromethylquinoline-3-carboxamido)-2-phenylacetyl, N-[2-(2-amino-4thiazolyl)acetyl]-D-phenylglycyl, 2-(6-bromo-1-ethyl-1,4-dihydro-4-oxothieno[2,3-d]pyridine-3-carboxamido)-2-phenylacetyl, 2-(4-ethyl-2,3-dioxo-1-piperazinocarboxamido)-2-thienylacetyl, 2-(4-n-pentyl-2,3-dioxo-1-piperazinocarboxamido)-2-thienylacetyl, 2-(4-n-octyl-2,3-dioxo-1-piper-azinocarboxamido)-2thienylacetyl, 2-(4-cyclohexyl-2,3-dioxo-1piperazinocarboxamido)-2-thienylacetyl, 2-[4-(2-phenylethyl)-2,3-dioxo-1-piperazinocarboxamido]-2-thienylacetyl, 2-(3-methylsulfonyl-2-oxoimidazolidine-1-carboxamido)-2-phenylacetyl, 2-(3-furfurylideneamino-2-oxoimidazolidine-1-carboxamido)-2-(4-hydroxyphenyl)acetyl, 2-(4-ethyl-2,3-dioxo-1-piperazinocarboxamido)-2-(4-benzyloxyphenyl) acetyl, 2-(4-ethyl-2,3-dioxo-1-piperazinocarboxamido)-2-(4-methoxyphenyl)acetyl, 2-(8-hydroxy-1,5-naphthyridine-7-carboxamido)-2-phenylacetyl, etc.

As the concrete examples of the acyl group representable by the formula $R^3$—$R^f$—CO—, are mentioned N-[2-(2-amino-4-thiazolyl)-2methoxyiminoacetyl]-D-alanyl, N-[2-(2-amino-4-thiazolyl)-2-methoxyiminoacetyl]-D-phenylglycyl, 2-(2-amino-4-thiazolyl)-2-[2-(2-amino-4-thiazolyl)-2-methoxyiminoacetamido]acetyl, 2-(2-chloroacetamido-4-thiazolyl)-2-methoxyiminoacetyl, 2-(2-amino-4-thiazolyl)-2-methoxyiminoacetyl,2-(2-amino-4-thiazolyl)-2-ethoxyiminoacetyl, 2-(2-amino-4-thiazolyl)-2-propoxyiminoacetyl, 2-(2-amino-4-thiazolyl)-2-butoxyiminoacetyl, 2-(2-amino-4-thiazolyl)-2-benzyloxyiminoacetyl, 2-(2-amino-4-thiazolyl)-2-allyloxyiminoacetyl, 2-(2-amino-5-chloro-4-thiazolyl)-2-methoxyiminoacetyl, 2-(2-amino-5-bromo-4-thiazolyl)-2-methoxyiminoacetyl, 2-(2-amino-4-thiazolyl)-2-oxyiminoacetyl, 2-thienyl-2-methoxyiminoacetyl, 2-furyl-2-methoxyiminoacetyl, 2-(1,2,4-thiadiazol-3-yl)-2-methoxyiminoacetyl, 2-(1,2,4-thiadiazol-5-yl)-2-methoxyiminoacetyl, 2-(1,3,4-thiadiazol-yl)-2-methoxyiminoacetyl, 2-(4-hydroxyphenyl)-2-methoxyiminoacetyl, 2-phenyl-2-methoxyiminoacetyl, 2-phenyl-2-oxyiminoacetyl, 2-[4-(γ-D-glutamyloxy)phenyl]-2-oxyiminoacetyl, 2-[4-(3-amino-3-carboxypropoxy)phenyl]-2-oxyiminoacetyl, etc.

As concrete examples of the acyl group representable by the formula

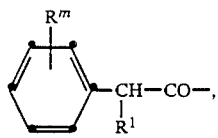

are mentioned α-sulfophenylacetyl, α-carboxyphenylacetyl, α-hydroxyphenylacetyl, α-ureidophenylacetyl, α-sulfoureido-phenylacetyl, α-sulfamoylphenylacetyl, α-phenoxycarbonyl-phenylacetyl, α-(p-tolyloxycarbonyl)phenylacetyl, α-formyloxyphenylacetyl, etc.

As concrete examples of the acyl group representable by the formula $R^n$—$R^o$—$CH_2$—CO—, are mentioned cyanoacetyl, acetoacetyl, phenylacetyl, phenoxyacetyl, 5-amino-5-carboxyvaleryl, 5-oxo-5-carboxyvaleryl, 4-carboxybutyryl, trifluoromethylthioacetyl, cyanomethylthioacetyl, 1H-tetrazolyl-1-acetyl, thienylacetyl, 2-(2-amino-4-thiazolyl) acetyl, 4-pyridylthioacetyl, 2-thienylthioacetyl, 3,5-dichloro-1,4-dihydro-4oxopyridine-1-acetyl, β-carboxyvinylthioacetyl, 2-(2-aminomethylphenyl)acetyl, etc.

The above-mentioned amino group and/or carboxyl group and/or hydroxyl group of the above-mentioned acyl group may optionally be protected.

As such amino-protecting groups are used groups similar to those representable by the afore-mentioned $R^b$. As carboxyl-protecting groups, are used any ones usually employable for protecting carboxyl group in the fields of β-lactam and organic chemistry. There are used, for example, ester residual groups and silyl groups, as more concretely exemplified by methyl, ethyl, n-propyl, isopropyl, tert-butyl, tert-amyl, benzyl, p-nitrobenzyl, p-methoxybenzyl, benzhydryl, 1-indanyl, phenacyl, phenyl, p-nitrophenyl, methoxymethyl, ethoxymethyl, benzyloxymethyl, acetoxymethyl, pivaloylmethyl, β-methylsulfonyl, β-trimethylsilylethyl, methylthiomethyl, trityl, β,β,β-trichloroethyl, β-iodoethyl, trimethylsilyl, dimethylsilyl, acetylmethyl, p-nitrobenzoylmethyl, p-mesylbenzoylmethyl, phthalimidomethyl, propionyloxymethyl, 1,1-dimethylpropyl, 3-methyl-3-butenyl, succinimidomethyl, 3,5-di-tert-butyl-4-hydroxybenzyl, mesylmethyl, benzenesulfonylmethyl, phenylthiomethyl, dimethylaminoethyl, pyridine-1-oxide-2-methyl, methylsulfinylmethyl, bis(p-methoxyphenyl)methyl, 2-cyano,-1,1-dimethylethyl, etc. As hydroxyl-protecting groups, are used any ones usually exployable for protecting hydroxyl group in the fields of β-lactam antibiotic, peptide and organic chemistry. They are, for example, ester residual groups such as acetyl, chloroacetyl, etc., esterified carboxyl groups such as β,β,β-trichloroethoxycarbonyl, β-trimethylsilylethoxycarbonyl, etc., ether residual groups such as tert-butyl, benzyl, p-nitrobenzyl, trityl, methylthiomethyl, β-methoxyethoxymethyl, etc., silyl ether residual groups such as trimethylsilyl, tert-butyldimethylsilyl, etc., acetal residual groups such as 2-tetrahydropyranyl, 4-methoxy-4-tetrahydropyranyl, etc., etc. The above-mentioned protecting groups can be optionally selected like in the cases of amino group and carboxyl groups.

As protecting groups other than the acyl groups representable by R, use is made of, for example, amino-protecting groups other than acyl groups, as employed as amino-protecting group representable by the aforementioned $R^b$.

The symbol Q in the formulae [I] and [II] stands for hydrogen atom or an ester residual group. As the ester residual group representable by Q, use is made of, for example, $C_{1-6}$ alkyl groups (e.g. methyl, ethyl, n-propyl, isopropyl, tert-butyl, tert-amyl, etc.), aralkyl* groups (e.g. benzyl, p-nitrobenzyl, p-methoxybenzyl, diphenylmethyl, bis(p-methoxyphenyl)methyl, etc.), etc.

The symbol Y in the formula [I] stands for the residual group of a nucleophilic compound. As the nucleophilic compound, use is made of, for example, one characterized by having nucleophilic nitrogen, carbon or sulfur, which has been widely described in various reports published so far concerning cephalosporin chemistry. For example, such reports published so far include the abovementioned British Patents Nos. 1544015, 2108114 and 2147900 and Belgian Patent No. 719,710. These nucleophilic compounds which have been known and used in the field of cephalosporin chemistry can widely be employed in the present invention.

The nucleophilic compound employable is exemplified by a sulfur nucleophilic compound, a nitrogen nucleophilic compound or a carbon nucleophilic compound. As the sulfur nucleophilic compounds (Y—H), a wide variety of known ones can be used. Among them, use is made of, for example, alkyl* thiol, allyl thiol, aryl* thiol, aralkyl* thiol, or a nitrogen-containing heterocyclic thiol having 1 to 5 nitrogen atoms having optionally having hetero-atoms other than nitrogen, selected from oxygen and sulfur. The nitrogen-containing heterocyclic thiol includes those having one to four substituents in the nucleus thereof. As such nitrogen-containing heterocyclic groups represented by Y, use is made of six-membered nitrogen-containing heterocyclic group e.g. pyridyl, N-oxidopyridyl, pyrimidyl, pyridazinyl, N-oxidopyridazinyl, triazinyl, quinazolinyl, etc. and condensed ring groups thereof, five-membered nitrogen-containing heterocyclic group e.g. imidazolyl, thiazolyl, thiadiazolyl, oxadiazolyl, triazolyl, tetrazolyl, etc. and condensed ring groups thereof. As the substituents on these nitrogen-containing heterocyclic groups, use is made of, for example, hydroxyl group, amino group, carboxyl group, oxo group, carbamoyl group, lower alkyl group (e.g. methyl, ethyl, trifluoromethyl, propyl, isopropyl, butyl, isobutyl, etc.), lower alkoxy group (e.g. methoxy, ethoxy, propoxy, butoxy, etc.), halogen atom (e.g. chlorine, bromine, etc.) or groups having various substituents through polyvalent groups such as $C_{1-3}$ lower alkylene group, —S—,

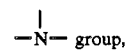
—N— group, etc. When the polyvalent groups are $C_{1-3}$ lower alkylene groups, said substituents may be mono- or di-lower alkylamino group, morpholino group, carboxyl group, sulfo group, carbamoyl group, alkoxycarbonyl group, lower alkylcarbamoyl group, alkoxy group, alkylthio group, alkylsulfonyl group, acyloxy group, morpholinocarbonyl group, etc., while when the polyvalent groups are —S— and

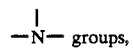
—N— groups, said substituents may be lower alkyl groups and lower alkylene groups having the above-mentioned substituents. When the polyvalent group is

—N—, an alkoxycarbonyl group, acyl group, carbamoyl group, lower alkylcarbamoyl group, etc. may further be bonded directly. Among these substituents on the nitrogencontaining heterocyclic groups more preferable examples are hydroxyl group, amino group, lower alkyl group mono- or di-lower alkylaminoalkyl group, sulfoalkyl groups. Use is concretely made of, for example, heterocyclic thiol such as pyridine thiol such as pyridine-2-thiol, pyrimidine thiol such as pyrimidine-2-thiol, methylpyridazine thiol, 4,5-dihydro-6-hydroxy-4-methyl-1,2,4-triazine-3-thiol, 2-methyl-5,6-dioxo-1,2,5,6-tetrahydro-1,2,4-triazine-3-thiol, imidazolethiol (e.g. imidazole-2-thiol), 1,3,4-thiadiazole-5-thiol, 1,2,3-thiadiazole-5-thiol, 2-methyl-1,3,4-thiadiazole-5-thiol, thiazolethiol, 5-methyl-1,3,4-oxadiazole-2-thiol, 1,2,3-triazole-5-triazole-5-thiol, 1-methyltetrazole-5-thiol, 1-(2-dimethylaminoethyl)tetrazole-5-thiol, 1-(2-sulfoethyl)tetrazole-5-thiol, 1-sulfomethyltetrazole-5thiol, benzimidazolethiol, benzthiazolethiol, benzoxazolethiol, etc. Besides, use is made of aliphatic, aromatic thiol e.g. methane thiol, ethane thiol, thiophenol, etc., thiourea, thiourea derivatives e.g. N-methyl thiourea, etc., thioamide derivatives e.g. thioacetamide, thiobenzamide, etc., thodanate e.g. potassium rhodanide, etc., thiocarboxylic acids e.g. thiosalicylic, dithiocarboxylic acids etc., thiocarbonates e.g. potassium ethylxanthate, potassium piperidine dithiocarbamate, etc. Among these sulfur nucleophilic compounds, the nitrogen-containing heterocyclic thiols are preferably employed. These sulfur nucleophilic compounds can be used for the reaction in the free form or a form of salt with the base at the acid radical thereof or a form of salt with the acid at the basic radical thereof. As the nitrogen nucleophilic compounds, a wide variety of known ones can be used. Among them, there may be, for example, mentioned metal salts of azide ion, (e.g. sodium azide) secondary or tertiary aliphatic, aromatic, and aroma-aliphatic amines and nitrogen-containing heterocyclic compounds such as dialkylamine (e.g. dimethylamine, diethylamine, etc.), trialkylamine (e.g. triethylamine, etc.), pyridine bases (pyridine and alkylpyridines, etc.), and a 5- to 7-membered heterocyclic compounds having two to five hetero-atoms selected from the group consisting of sulfur oxygen and nitrogen, at least one of the hetero-atoms being nitrogen, such as pyrimidines, morpholines, purines, pyridazines, pyrazines, pyrazoles, imidazoles, triazoles and tetrazoles, condensed heterocyclic compounds in which two or more, preferably two to three, such heterocyclic rings are orthocondensed or ortho-peri-condensed, such as imidazopyridines, imidazopyridazines and cycloalkenopyridines.

As preferable nitrogen nucleophilic compounds are employed those representable by the formula

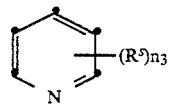  [X]

[wherein $n_3$ denotes an integer of 0 to 5, and $R^s$ (when $n_3$ is 2 to 5, $R^s$'s may be the same as or different from each other, or they may form, together with carbon atoms they are attached to, a 5 to 7-membered saturated or unsaturated condensed ring) stands for aliphatic group such as lower alkyl (methyl, ethyl, n-propyl, iso-propyl, etc.) etc., aryl group such as phenyl, etc., aroma-aliphatic group such as phenyl lower alkyl (benzyl, phenylethyl, etc.), etc. or alkoxymethyl such as methoxymethyl, ethoxymethyl, n-propoxymethyl, iso-propoxymethyl, etc., or acyloxymethyl such as alkanoyloxymethyl e.g. acetoxymethyl, etc., cyano, formyl, carbamoyl, acyloxy such as alkanoyloxy e.g. acetoxy, etc., esterified carboxy, alkoxy such as methoxy, ethoxy, n-propoxy, iso-propoxy, etc., aryloxy such as phenoxy, etc., aralkolxy such as benzyloxy, etc., alkylthio such as methylthio, ethylthio, etc., arylthio, aralkylthio, hydroxy, N-mono $C_{1-6}$ lower alkylcarbamoyl such as N-methylcarbamoyl, N-ethylcarbamoyl, etc., N,N-di-lower alkyl carbamoyl such as N,N-dimethylcarbamoyl, N,N-diethylcarbamoyl, etc., N-(hydroxy lower alkyl)carbamoyl such as N-(hydroxymethyl)carbamoyl, N-(hydroxyethyl)-carbamoyl, etc., carboxy lower alkyl such as carboxymethyl, etc. or carbamoyl lower alkyl such as carbamoyl methyl, carbamoyl ethyl, etc.].

Among the substituents representable by $R^s$ mentioned above, more preferable examples are $C_{1-6}$ alkyl, $C_{2-7}$ alkoxymethyl cyano, formyl, carbamoyl, $C_{1-6}$ alkyl and carbamoyl $C_{1-6}$ alkyl.

As further examples of preferable nitrogen nucleophilic compounds are employed those representable by the formula

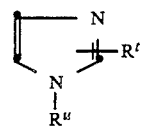  [XI]

[wherein $R^t$ and $R^u$ each stand for hydrogen atom or the group defined by $R^s$, or $R^t$ and $R^u$ are bonded to each other and form, together with the carbon and nitrogen atoms they are each attached to, a saturated or unsaturated 5 to 7-membered heterocyclic ring having one to five hetero-atoms selected from among sulfur, oxygen and nitrogen, one to four of the hetero-atoms being nitrogen, which is exemplified by pyridine, pyridazine, pyrimidine, pyrazine, thiazole, oxazole, imidazole, tetrazole, triazole, thiadiazole, triazine, etc., then to form a condensed heterocyclic ring]. Specific embodiments are, for example, nitrogen-containing heteroxyclic compounds, such as pyridine, nicotinic acid, nicotinamide, isonicotinamide, pyridine-sulfonic acid, pyridylacetic acid, pyrazine, 2-carbamoyl pyrazine, pyrimidine imidazole, 1-methyl imidazole, 2,3-cyclopentenopyridine, methyl nicotinate, imidazo [1,2-a]pyridine, imidazo[1,5-a]pyridine, imidazo[1,2-b pyridazine, 1-methylpyrrolidine, 2-(4-pyridyl)ethanesulfonic acid, 5-methyl tetrazole, etc.

As the carbon nucleophilic compounds are employed, for example, inorganic cyanides (e.g. sodium cyanide), pyrroles and condensed pyrroles (e.g. indoles), etc.

The dotted lines in the formulae [I] and [II] show that the double bond at the cephem ring is located at the 2-position

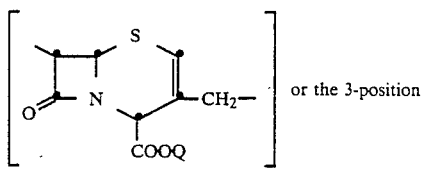 or the 3-position

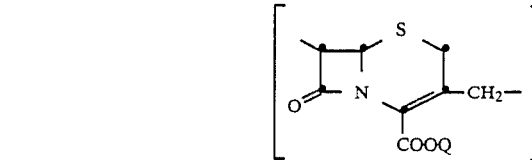

In the trivalent phosphorus compounds representable by the formula [III], $R^1$, $R^2$ and $R^3$ respectively stand for hydrocarbon group whose carbon number is not more than 8, and any of the two of them may be combined to each other to form polymethylene group. As hydrocarbon groups shown by $R^1$, $R^2$ and $R^3$ are mentioned, for example, alkyl* group, alkenyl* group, cycloalkyl* group, aryl* group, aralkyl* group, etc., whose carbon number is not more than 8. As preferable hydrocarbons shown by $R^1$ are used, for example, $C_{1-8}$ alkyl such as, $C_{1-6}$ alkyl mentioned above, heptyl, octyl, etc., $C_{5-8}$ aralkyl e.g. benzyl, phenethyl, furfuryl, etc., $C_{2-8}$alkenyl e.g. allyl, 2-butenyl, 3-butenyl, etc., and these $C_{1-8}$alkyl groups, $C_{5-8}$ aralkyl groups and $C_{2-8}$alkenyl groups may have 1 to 3 substituents. As examples of those substituents are mentioned those described in the foregoing about the substituents of alkyl, aralkyl and alkenyl groups of $R^a$ to $R^o$. As preferable examples of hydrocarbon groups representable by $R^2$ and $R^3$ are employed, for example, besides for example $C_{1-8}$alkyl groups, $C_{5-8}$aralkyl groups and $C_{2-8}$alkenyl groups described in respect of $R^1$, $C_{5-10}$ aryl groups e.g. phenyl, naphthyl, furyl, etc. These $C_{5-10}$aryl groups may have 1 to 3 substituents which are exemplified by those described in respect of $R^a$ to $R^o$. In the compounds of the formula [III], any two of $R^1$, $R^2$, and $R^3$ may be bonded to each other to form polymethylene group e.g. dimethylene, trimethylene, etc. As specific examples of such trivalent phosphorus compounds [III] are mentioned phosphorous triester, phosphonous acid diester, phosphinous acid ester, etc. The phosphorous triester was exemplified by trimethyl phosphite, triethyl phosphite, triisopropyl phosphite, tri-n-butyl phosphite, isooctyl phosphite, tris(2-ethylhexyl)phosphite, tris(2-chloroethyl)phosphite, etc., and those described on "Organic Phosphorus Compounds", Vol. 5, pp.157 to 194 (1973). The phosphonous acid diester is exemplified by, besides phenyl phosphonous acid dimethylester, phenyl phosphonous acid diethylester, etc., those described on "Organic Phosphorus Compounds", Vol. 4, pp.361 to 391 (1972). The phosphinous acid ester (phosphinite) is exemplified by, besides diethylphosphinic acid methylester, diphenylphosphinic acid ethylester, etc., those described on "Organic phosphorus Compounds" Vol. 4, pp.513 to 517 (1972). These phosphorus compound [III] can be synthesized by a known method or by a method analogous to a known method, and they can be used for the method of this invention as isolated or they as the reaction mixture. Among the phosphorus compounds [III], the ones wherein $R^1$, $R^2$ and $R^3$ are independently $C_{1-8}$ alkyl are preferred, and further, among them trimethyl phosphite, triethyl phosphite, triisopropyl phosphite or tri-n-butyl phosphite are preferable. Moreover, phosphorous acid triester such as trimethyl phosphite or, triethyl phosphite, for example, which is industrially produced as a flame retarder of plastic and wood and an additive for gasoline and paint, is readily available and can be used for advantageously especially for the present invention. In the method of this invention, the end product [I] can be produced by allowing a compound [II] to react with a nucleophilic compound and a trivalent phosphorus compound [III].

Compounds [II] include not only those whose acid radicals such as carboxyl group, sulfo group, etc. contained in R and Q are in the free form but also the salts thereof with non-toxic cation of sodium, potassium, etc., an organic amine e.g. triethylamine, tri-n-butylamine, di-n-butylamine, dicyclohexylamine, pyridine, collidine, 2, 6-lutidine, etc. And, when R and Q contain a basic group, a salt with an organic acid such as acetic acid, tartaric acid, methanesulfonic acid, etc., and a salt with an inorganic acid such as hydrochloric acid, hydrobromic acid, sulfuric acid, phosphoric acid, etc. may be formed, and such salts as well as intramolecular salts formed by, for example a quaternary ammonium group contained in R or Y and its counter ion from an acid radical e.g. carboxyl group, are included in the starting compounds [II]. The nucleophilic compounds can, depending on the kinds, take the form of salts preferably non-toxic salts, with a base or of salts, preferably non-toxic salts, with an acid, and both the salts are included in the materials of this invention. As these salts with bases and acids are used, for example, those described in respect of compounds [II].

The order of mixing a compound [II], a nucleophilic compound and a compound [III] is not especially limited, and, usually, in an organic solvent, a phosphorus compound [III] or an organic solvent solution thereof is added to a mixture of [II] and a nucleophilic compound, or, in an organic solvent, a compound [II] or an organic solvent solution thereof is added a mixture of a nucleophilic compound and a phosphorus compound.

The molar ratios of a nucleophilic compound and a phosphorus compound [III] relative to a compound [II] are preferably 1.0 times or more, usually 1.0 times to ten times, respectively. A nucleophilic compound or a phosphorus compound [III] per se can be used as a reaction solvent, but, usually, a nucleophilic compound is used in an amount of 1.0 to 10.0 times relative to a compound [II], preferably 1.0 to 5.0 times and a phosphorus compound is used in an amount of 1.0 to 5.0 times, preferably 1.0 to 3 .0 times relative to a compound [II].

Organic solvents to be employed for this reaction may be any ones which are inert to the reaction, which are exemplified by amides such as formamide, dimethylformamide, dimethylacetamide, etc., halogenated hydrocarbons such as chloroethane, isobutyl chloride, methylene chloride, chloroform, 1,2-dichlorethane, carbon tetrachloride, 1,1,1-trichloroethane, 1,1,2-trichloroethane, 1,1,2,2-tetrachloroethane, fluorobenzene, dichlorobenzene, etc., ethers such as diemthyl ether, diethyl ether, tetrahydrofuran, dioxane, etc., esters such as methyl acetate, ethyl acetate, isobutyl acetate, methyl propionate, ethylene carbonate, etc., nitriles such as acetonitrile, propionitrile, benzonitrile, etc., nitro compounds such as nitromethane, nitroethane, etc., ketones such as acetone, methyl ethyl ketone, etc., hydrocarbons such as benzene, toluene, mesitylene, etc., alcohols such as methanol, ethanol, propanol, butanol, etc., acids such as acetic acid, propionic acid, etc., etc. and these may be used as a suitable mixture. Especially, use of, for example, methylene chloride, acetonitrile, formamide, a mixture solvent of formamide and acetonitrile, a mixture solvent of methylene chloride and acetonitrile, a mixture solvent of methylene chloride and tetrahydrofuran, etc. brings about a favorable result.

This reaction proceeds more promptly when an acid component is present in the reaction mixture. In the compound [II], when Q is hydrogen, i.e. when "—COOQ" is a carboxyl group, the reaction is usually completed in a short period of time due to its acidity, while when Q is ester residue, in the form of a salt with cation of sodium, potassium etc. or organic amine, and when the acidity of carboxyl group is neutralized due to a basic group such as amino group, etc. contained in the structure of the compound [II] or the nucleophilic compound, the reaction requires a relatively long period of time. In such cases, the reaction can be conducted by adding an acid so as to shorten the reaction time. As the acid to be used for such purpose may by any one which does not give unfavorable effects on the reaction, as exemplified by carboxylic acid such as formic acid, acetic acid, propionic acid, butyric acid, valeric acid, benzoic acid, etc., sulfonic acids such as methane sulfonic acid, benzene sulfonic acid, p-toluene sulfonic acid, etc., hydrogen halogenides such as hydrogen chloride, hydrogen bromide, etc., Lewis acids such as boron trifluoride, zinc chloride, aluminium chloride, etc., etc. Among them, carboxylic acids such as acetic acid are used especially preferably. The reaction temperature and time may be suitably selected depending on the kinds of compounds [II], nucleophilic compounds, phosphorus compounds [III] and solvents. However, the reaction time is usually a minute to about ten hours. The reaction may be conducted in a broad temperature range from −20° C. to 80° C. In general, the reaction time can be shortened by raising the temperature, but the reaction is usually conducted at room temperature or under slight cooling (0 to 30° C.) for the purpose of avoiding the decomposition of the cephalosporins due to heating. The reaction is usually completed under mild conditions, at 15 to 30° C. for several minutes to several hours.

In the method of this invention, as the reaction proceeds, the ester-linkage of a phosphorus compound [III] is hydrolized to produce corresponding alcohols, and the reaction can be allowed to proceed while eliminating such alcohols by, for example, azeotropic distillation under reduced pressure with the organic solvent then employed.

Cephalosporin compound [I] thus obtained can be isolated from the reaction mixture by for example, when desired, subjecting an excess amount of the phosphorus compound then employed to, for example, hydrolysis, followed by subjecting the resultant product to per se conventional means such as filtration, solvent extraction. pH change, phase transfer, salting out, crystallization, recrystallization, chromatography, etc. And, depending on the kinds of the acyl group shown by R, [I] can be led to 7-amino cephem compound (compound [I] where R is hydrogen atom), which is a useful intermediate for preparing an antibiotic substance, by adding to the reaction mixture, without isolating [I], dimethyl aniline, trimethyl silyl chloride, phosphorus pentachloride, methanol and water in sequence to thereby cleave the acyl group at 7-position by a known method or a method analogous to known method. When the object compound [I] is in the free form, it may be modified into a salt by per se conventional manner, which is included in the object compounds of the formula [I]. As the salts of the object compound [I], preferably non-toxic salts such ones as described in respect of the starting compound [II] are mentioned, which are, for example, salts at the acid radical with an alkali metal e.g. lithium, sodium, potassium, etc., an alkaline earth metal e.g. calcium, magnesium, etc. amines e.g. di-n-butylamine, dicyclohexylamine, diisobutylamine, di-tert-butylamine, triethylamine, pyridine, 2,6-lutidine, tributylamine, etc., and salts at the basic radical with a mineral acid e.g. hydrochloric acid, sulfuric acid, etc., an organic acid e.g. oxalic acid, acetic acid, formic acid, trichloroacetic acid, trifluoroacetic acid, etc., sulfonic acid e.g. methanesulfonic acid, toluenesulfonic acid, naphthalenesulfonic acid, camphor sulfonic acid, etc., phosphoric acid e.g methylphosphoric acid, dimethylphosphoric acid, diphenylphosphoric acid, etc., phosphonic acid e.g. phenylphosphonic acid, etc.

Incidentally, the starting compounds [II] employable in the present invention can be prepared by, for example, a fermentative method [e.g. methods described on Nature Vol. 246, p.154 (1973), Japanese Patent Application Laid-Open No., 491/1974, etc.] or by subjecting the product obtained by the fermentative method to chemical or enzymatic treatment [e.g. methods described in Biochemical Journal Vol. 81, pp.591–596 (1961)]. And, the nucleophilic compounds can be synthesized by a known method, e.g. a method described on, "Heterocyclic Compounds" compiled by Robert C. Elderfield, "The Chemistry of Heterocyclic Compounds", compiled by Weissberger et al., J. Heterocyclic Chemistry Vol. 15, p.1295 (1978), J. Pharmaceutical Sciences Vol. 51, pp. 862–864 (1962), Japanese Patent Application Laid-Open No. 231684/1985 or methods analogous thereto.

The antibacterial compounds [I] wherein R is an acyl can be used as antibiotic substances having excellent antibiotic properties when used in accordance with known methods [e.g. methods described on Japanese Patent Applications Laid-Open No. 72286/1974, 48996/1977 and 1280/1978 etc.], and the compounds [I] can also be used as intermediates for antibiotic substances having excellent antibiotic potency. For example, a compound [I] embraces 7-[2-(2-imino-4-thiazolin-4yl) acetamido] compound [described on e.g. USP 4,080498, etc.] which can be obtained by first subjecting the compound [I] wherein R is for example a group of the formula

to a per se conventional method [e.g. Japanese Patent Application Publication Nos. 41-13862/1966 40899/1970, Laid-Open No. 34387/1972, USP 3.632, 578, etc.] and to cleave the acyl group at 7-position, then allowing the resultant to react with 4-halogeno-3-oxobutyrylamido-compound, followed by allowing the resultant to react with 4-halogeno-3-oxobutyrylamido-compound, followed by allowing the resultant to react with thiourea. All of the thus-obtained antibacterial compounds show excellent antibiotic properties, though the properties are somewhat different among them depending on the kinds of substituents at 3-position.

The following examples are intended to illustrate this invention in further detail and should by no means be construed as limiting the scope of the present invention.

Symbols used in the examples are of the following meaning.

s: singlet, br: broad, d: doublet, dd: double doublet, t: triplet, q: quartet, ABq: AB type quartet, m: multiplet, D$_2$O: deuterium oxide, %: weight %, TLC: thin layer chromatography, DMSO—d$_6$: dimethyl sulfoxide—d$_6$, NaHCO$_3$: sodium hydrogencarbonate NMR (nuclear magnetic resonance spectrum) was, unless otherwise specified, shown in terms of the chemical shift values [δ(ppm)] obtained by using, as internal standards, tetramethylsilane (when DMSO—d$_6$ was used as the solvent) or sodium 2,2-dimethyl-2-silapentane-5-sulfonate (when D$_2$O was used as the solvent). "Room temperature" means a temperature between about 5 and 35° C.

EXAMPLE 1

To 5.03 g of 7β-D-5-carboxy-5-phthalimidovaleramido)-3-cephem-4-carboxylic acid were added 100 ml of tetra-hydrofuran-methylene chloride mixture solution (1:2,v/v), 1.74 g of 5-mercapto-1-methyl-1H-tetrazole and 2.3 ml of trimethyl phosphite in sequence. The reaction was allowed to proceed at 18 to 22° C. for 3.5 hours while stirring. To the reaction solution was added 30 ml of 1N HCl, and the mixture was stirred for 30 minutes, which was concentrated under reduced pressure to about 30 ml. To the concentrate was added 30 ml of methylene chloride, to which was added 1N NaOH to render the pH to 5.6, followed by separating the organic layer from the aqueous layer. To the aqueous layer was added 30 ml of tetrahydrofuran-methylene chloride mixture solution (1:1,v/v), whose pH was changed to 2.0 with 2N HCl, then the organic layer was separated. The aqueous layer was subjected to extraction with 30 ml of the same mixture solution. The organic layers were combined, washed with saturated aqueous saline solution and dried on anhydrous magnesium sulfate, followed by concentration under reduced pressure. The concentrate was poured into 300 ml of ether and the precipitating matter was collected by filtration, washed with ether and dried to obtain 5.86 g (yield:97.4%) of 7β-D-5-carboxy-5-phthalimidovaleramido)-3-(1-methyl-1H-tetrazol-5-yl) thiomethyl-3-cephem-4-carboxylic acid as white powder.

IR(KBr): 3350,2950,1773,1713,1530 cm$^{-1}$

NMR(DMSO–d$_6$): δ1.20–2.40(6H,m,—(CH$_2$)$_3$—), 3.60(2H,br,2—CH$_2$), 3.94(3H,s,—CH$_3$),4.27(2H,br,3—CH$_2$),4.27(1H,t,J=8 Hz, >CH—),5.00(1H,d,J=5 Hz,C$_6$—H),5.61(1H,dd,J=8×5 Hz,C$_7$—H),7.89(4H,s,C$_6$H$_4$<),8.76(1H,d,J=8 Hz,—CONH—)ppm

EXAMPLE 2

To 2.52 g of 7β-(D-5phthalimidovaleramido)-3-hydroxymethyl-3-cephem-4-carboxylic acid were added 20 ml of methylene chloride, 0.99 g of 5-mercapto-2-methyl-1,3,4-thiadiazole and 1.7 ml of triethyl phosphite in sequence. The mixture was stirred at room temperature for 3.0 hours. To this reaction solution was added 10 ml of 1N HCl, which was stirred for 30 minutes at 20 to 25° C.; the pH was adjusted to 6.0 with 1N NaOH, followed by separating into two layers. To the aqueous layer were added 20 ml of tetrahydrofuran and 20 ml of methylene chloride; the pH was adjusted to 2.0 with 2N HCl, followed by separating into two layers. The aqueous layer was subjected to extraction with a mixture of 20 ml of tetrahydrofuran and 20 ml of methylene chloride. The organic layers were combined and dried on anhydrous magnesium sulfate, which was concentrated under educed pressure, followed by addition of 150 ml of ether. Resultant powder was collected by filtration, washed with ether, then dried under reduced pressure to obtain 2.87 g (yield: 92.9%) of 7β-(D-5-carboxy-5-phthalimidovaleramido)-3-(2-methyl-1,3,4-thiadiazol-5-yl) thiomethyl-3-cephem-4-carboxylic acid as white powder.

IR(KBr): 3330,2920,1775,1715,1530 cm$^{-1}$

NMR(DMSO—d$_6$): δ1.30–2.40(6H,m,—(CH$_2$)$_3$—), 2.71(3H,s,—CH$_3$),3.62(2H,ABq,J=18 Hz,2—CH$_2$), 4.37(2H,ABq,J=14 Hz,3—CH$_2$),4.76(1H,t,J=7 Hz, >CH—),5.07(1H,d,J=5 Hz,C$_6$—H),5.65(1H,dd,J=8×5 Hz,C$_7$—H),7.92(4H,s,C$_6$H$_4$<),8.81(1H,d,J=8 Hz,CONH)ppm

EXAMPLE 3

To 580 mg of dipotassium 7β-D-5-carboxy-5-phthalimidovaleramido)-3-hydroxylmethyl-3-cephem-4-carboxylate were added 4.0 ml of glacial acetic acid, 151 mg of 5-mercapto-1-methyl-1H-tetrazole and 0.50 ml of triethyl phosphite in sequence. The reaction was allowed to proceed at 25±2° C. for 30 minutes under stirring. To the reaction solution was added 50 ml of ether, and then precipitating powder was collected by filtration, which was washed with ether, followed by drying under reduced pressure to obtain 0.78 g of white powder. The powder was suspended in 8 ml of water, whose pH was adjusted to 2.0 with 4N HCl. Resultant precipitates were collected by filtration, washed with water and dried under reduced pressure to obtain 550 mg (yield: 91.4%) of 7β-(D-5-carboxy-5-phtalimidovaleramido)-3-(1-methyl-1H-tetrazol-5-yl) thiomethyl-3-cephem-4-carboxylic acid as white powder. IR and NMR spectra of this product were in agreement with those in Example 1.

EXAMPLE 4

In a mixture of 2.0 ml of formamide and 1.0 ml of acetonitrile was dissolved 232 mg of 5-mercapto-1-methyl-1H-tetrazole. To this solution were added 580 mg of dipotassium 7β-(D-5-carboxy-5-phthalimidovaleramido)-3-hydroxymethyl-3-cephem-4-carboxylate and 0.50 ml of triethyl phosphite in sequence. The mixture solution was warmed to 30° C. in about one minute. The reaction was allowed to proceed at 80±3° C. for 9 minutes under stirring. The reaction solution was cooled on an ice-water bath, to which was added 3 ml of 1N HCl. The mixture was stirred for 30 minutes, followed by concentration under reduced pressure. To the concentrate were added 20 ml of water, 10 ml of tetrahydrofuran and 10 ml of methylene chloride. The mixture was shaken and left standing to form two layers. The organic layer was separated, and the aqueous layer was subjected to extraction with a mixture of 10 ml of tetrahydrofuran and 10 ml of methylene chloride. The organic layers were combined, washed with 10 ml of water and dried over anhydrous magnesium sulfate, followed by concentration under reduced pressure. To the concentrate was added 50 ml of ether, then resultant precipitates were collected by filtration, followed by drying under reduced pressure to obtain 504 mg (yield: 83.8%) of 7β-(D-5-carboxy-5-phthalimidovaleramido)-3-(1-methyl-1H-tetrazol-5-yl) thiomethyl-3-cephem-4-carboxylic acid as white powder. The IR and NMR spectra of this product were in agreement with those in Example 1.

EXAMPLE 5

In a mixture of 2.0 ml of formamide and 8.0 ml of acetonitrile was dissolved 0.522 g of 5-mercapto-1-methyl-1H-tetrazole. To the solution were added in sequence 1.43 g of 7β-(D-5-benzamido-5-carboxyvaleramido)-3-hydroxymethyl-3-cephem-4-carboxylic acid and 1.1 ml of trimethyl phosphite, and the mixture was stirred at 20 to 25° C. for 60 minutes. To the reaction solution were added 3 ml of 2N HCl and 50 ml of water, and the mixture was stirred for 30 minutes, followed by concentration under reduced pressure. To the concentrate was added 40 ml of a mixture of tetrahydrofuran and methylene chloride (1:1,v/v), which was allowed to form two layers. The aqueous layer was separated and subjected to extraction with 20 ml of the same mixture. The organic layers were combined, washed with 15 ml of water and dried over anhydrous magnesium sulfate, followed by concentration under reduced pressure. To the concentrate was added ether, and resulting powder was collected by filtration, followed by drying under reduced pressure to give 1.62 g (yield: 93.8%) of 7β-(D-5-benzamido-5-carboxyvaleramido)-3(1-methyl-1H-tetrazol-5-yl) thiomethyl-3-cephem-4-carboxylic acid.

IR(KBr): 3300,2950,1780,1720,1645, 1530 cm$^{-1}$
NMR(D$_2$O—NaHCO$_3$): δ1.5–2.6(6H,m,—(CH$_2$)$_3$), 3.41(2H,ABq,J=17 Hz,2—CH$_2$),4.00(3H,s,—CH$_3$), 4.15(2H,ABq,J=14 Hz,3—CH$_2$),4.44(1H,br,->CH—),
5.20(1H,d,J=5 Hz,C$_6$—H),5.56(1H,d,J=5 Hz,C$_7$—H),7.3–8.2(5H,m,C$_6$H$_5$—)ppm

EXAMPLE 6

To a mixture of 3.53 g of 7-(D-5-carboxy-5-phthalimidovaleramido)-3-hydroxymethyl-3-cephem-4-carboxylic acid ditriethylamine salt and 1.45 g of 5-mercapto-1-methyl-1H-tetrazole were added in sequence 20 ml of acetonitrile and 4.66 g of tributyl phosphite. The reaction was allowed to proceed at 20 to 22° C. for 60 minutes. To the reaction solution was added 70 ml of water, then most of the acetonitrile was distilled off under reduced pressure. To the residue was added 30 ml of methylene chloride, to which was added 1N NaOH to change the pH to 8.5 to allow the precipitates to be dissolved. To the solution was added 2N HCl to change the pH to 5.6, then the solution was made to form two layers. To the aqueous layer was added 60 ml of a mixture of tetrahydrofuran-methylene chloride (1:1,v/v), to which was added 2N HCl to change the pH to 2.0, then the solution was made to form two layers. The organic layer was separated, and the aqueous layer was subjected to extraction with 40 ml of the same mixture solvent. The organic layers were combined, washed with 20 ml of water and dried over anhydrous magnesium sulfate, followed by concentration under reduced pressure. To the concentrate was added 140 ml of ether, and resulting precipitates were collected by filtration, then washed with ether, followed by drying under reduced pressure to obtain 2.86 g (yield: 95.1%) of 7β-(D-5-carboxy-5-phthalimidovaleramido)-3-(1-methyl-1H-tetrazol-5-yl) thiomethyl-3-cephem-4-carboxylic acid as white powder. The NMR spectrum of this product was in agreement with that in Example 1.

EXAMPLE 7

To 0.543 g of 1-(2-dimethylaminoethyl)-5-mercapto-1H-tetrazole hydrochloride were added 6.0 ml of formamide and 6.0 ml of acetonitrile to make a solution. The solution was added to 1.00 g of 7β-(D-5-carboxy-5-phthalimidovaleramido)-3-hydroxymethyl-3-cephem-4-carboxylic acid, followed by addition of 0.50 ml of trimethyl phosphite. The reaction was allowed to proceed at 20 to 25° C. while stirring for 2.0 hours. To the reaction solution were added 30 ml of acetonitrile and 50 ml of ether to cause precipitation of a resinous substance. The supernatant was removed by decantation, and the resinous substance was washed with 20 ml of acetone. To the resultant were added in sequence 10 ml of ethanol, 50 ml of ether and 2.5 ml of ether solution of hydrogen chloride (2 mol./l). The mixture was stirred, and the resulting powder was collected by filtration, washed with ether, and dried under reduced pressure to obtain 1.27 g (yield: 92.0%) of 7β-(D-5-carboxy-5-phthalimidovaleramido)-3-[1-(2-dimethylaminoethyl)-1H-tetrazol-5-yl] thiomethyl-3-cephem-4-carboxylic acid hydrochloride as white powder.

IR(KBR): 3140,3030,1773,1713,1530 cm$^{-1}$
NMR(DMSO—d$_6$—D$_{20}$): δ1.3–2.4(6H,m, —(CH$_2$)$_3$—),2.92(6H,s,—CH$_3$×2),3.5–3.9(4H,m,2—CH$_2$—CH$_2$N<),4.30(2H,br,3—CH$_2$),4.5–4.9(3H, m,—CH$_2$CH$_2$N< and >CH—),5.03(1H,d,j=5 Hz,C$_6$—H), 5.58(1H,d,J=5 Hz,C$_7$—H),7.92(4H,s,C$_6$H$_5$—)ppm

EXAMPLE 8

To a solution of 1.31 g of 7β-(D-5-carboxy-5-phenoxycarbonylaminovaleramido)-3-hydroxymethyl-3-cephem-4-carboxylic acid in a mixture solution of tetrahydrofuran (5.0 ml)-methylene chloride (5.0 ml) was added 0.33 g of pyridine dissolved in 2.0 ml of tetrahydrofuran, followed by addition of 0.70 ml of trimetyl phosphite. The resultant was stirred at 20 to 25° C. for 2.0 hours. Precipitating powder was collected by filtration, which was washed with 10 ml of tetrahydrofuran-methylene chloride mixture solution (1:1,v/v) and 10 ml of methylene chloride. The resultant product was dissolved in 6.0 ml of acetonitrile-water (4:1,v/v). The solution was subjected to a silica gel chromatography, using acetonitrile-water (4:1) as the eluent. The eluate was subjected to TLC (developed with a solvent, acetonitrile 15:water 5:99% formic acid 0.25, using silica gel plate 60F-254, manufactured by E. Merck, and detected with UV). Fractions showing a spot at Rf 0.27 were collected, concentrated under reduced pressure, followed by freeze-drying to obtain 1.21 g (yield: 82.3%) of 7β-(D-5-carboxyl-5-phenoxycarbonylaminovaleramido)-3-(1-pyridinio) methyl-3-cephem-4-carboxylate as white powder.

IR(KBr): 3370,3040,1775,1725,1660, 1610 cm$^{-1}$
NMR(D$_2$O—NaHCO$_3$): δ1.78(4H,br,—CH$_2$CH$_2$—), 2.39(2H,br,CH$_2$CO),3.30(2H,ABq,J=18 Hz,2—CH$_2$), 4.02(1H,br,>CH—),5.15(1H,d,J=5 Hz,C$_6$—H), 5.40(2H,ABq,J=14 Hz,3—CH$_2$),5.65(1H,d,J=5 Hz, C$_7$—H),7.1–7.6(5H,m,C$_6$H$_5$—),7.8–9.0(5H,m, Pyridine)ppm

EXAMPLE 9

To 4.93 g of 7β-(D-5-carboxy-5-phenoxycarbonylaminovaleramido)-3-hydroxymethyl-3-cephem-4-carboxylic acid were added 80 ml of tetrahydrofuran-methylene chloride mixture solution (1:2,v/v) and 1.74 g of 5-mercapto-1-methyl-1H-tetrazole. The mixture was stirred for 5 minutes, to which was added 3.7 ml of trimethyl phosphite, followed by stirring at 20 to 25° C. for 3hours. To the reaction solution was added 21 ml of water, whose pH was rended to 2.0 with 4N HCl, which was made to form two layers. The aqueous layer was subjected to separation into two layers twice using a mixture of 10 ml of tetrahydrofuran and 20 ml of methylene chloride. The organic layers were combined, washed with aqueous saline, dried over anhydrous magnesium sulfate, followed by concentration under reduced pressure. To the concentrate was added ether, and the solid matter was crushed, then resulting powder was collected by filtration. Thus collected powdery product was washed with ether and subjected to drying under reduced pressure to obtain 5.23 g (yield: 88%) of 7β-(D-5-carboxy-5-phenoxycarbonylaminovaleramido)-3-(1-1H-tetrazol-5-yl) thiomethyl-3-cephem-4-carboxylic acid.

IR(KBr): 3270,3020,2920,1780,1725, 1530 cm$^{-1}$
NMR(DMSO—d$_6$): δ1.4–2.4(6H,m,—(CH$_2$)$_3$), 3.69(2H,br,2—CH$_2$),3.94(3H,s,CH$_3$),4.30(2H,br, 3-CH$_2$),5.05(1H,d,J=5 Hz,C$_6$—H),5.65(1H,q,J=5 ×8 Hz,C$_7$—H),6.9–7.6(5H,m,C$_6$H$_5$—),8.03(1H,d,J=8 Hz,OCONH),8.83(1H,d,J=8 Hz,CONH)ppm

EXAMPLE 10

To 4.77 g of 7β-[D-5-(p-tert-butylbenzamido)-5-carboxyvaleramido]-3-hydroxymethyl-3-cephem-4-carboxylic acid were added 80 ml of tetrahydrofuran-methylene chloride mixture solution (1:2,v/v), 1.74 g of 5-mercapto-1-methyl-1H-tetrazole and 4.15 g of triethyl phosphite. The mixture was stirred at 20 to 25° C. for 3 hours, followed by subjecting to after-treatment similar to that in Example 9 to give 5.71 g (yield: 90%) of 7 [D-5-(p-tert-butylbenzamido)-5-carboxyvaleramido]-3-(1-methyl-1H-tetrazol-5-yl) thiomethyl-3-cephem-4-carboxylic acid.

IR(KBr): 3300,2960,1780,1725,1640, 1535 cm$^{-1}$

NMR($D_2O$—NaHCO$_3$): δ1.23(9H,s,CH$_3$×3),1.98 (4H,br,—CH$_2$CH$_2$—),2.43(2H,br,CH$_2$CO),3.34(2H, ABq,J=17 Hz,2—CH$_2$),4.00(3H,s,N—CH$_3$),4.16(2H, ABq,J=14 Hz,3—CH$_2$),5.01(1H,d,J=5 Hz,C$_6$—H), 5.60(1H,d,J=5 Hz,C$_7$—H), 7.65(4H,dd,J=8 Hz,—C$_6$H$_4$—)ppm

EXAMPLE 11

In a mixture of 2 ml of formamide and 4 ml of acetonitrile was dissolved 633 mg of 2-carboxymethylthio-5-mercapto-1,3,4-thiadiazole at about 40° C. The solution was cooled to about 30° C., to which were added in sequence 0.31 ml of trimethyl phosphite, 689 mg of tributylamine salt of 7β-(D-5-carboxy-5-phthalimidovaleramido)-3-hydroxymethyl-3-cephem-4-carboxylic acid and 0.20 ml of ether solution of hydrogen chloride (5mol./l). The mixture was stirred at 20 to 25° C. for one hours, to which was added 20 ml of water. Acetonitrile was distilled off under educed pressure. To the residue was added 10 ml of tetrahydrofuran, whose pH was rendered to 2.6with 4N HCl. To the resultant was added 15 ml of methylene chloride to allow the mixture to form two layers. The aqueous layer was taken, to which were added 10 ml of tetrahydrofuran and 15 ml of methylene chloride, then resulting organic layer was separated. The organic layers were combined and washed with aqueous saline and dried over anhydrous magnesium sulfate, then the solvent was distilled off. The residue was subjected to a silica gel chromatography to obtain 580 mg (yield: 81%) of 7β-(D-5-carboxy-5-phthalimidovaleramido)-3-(2-carboxymethylthio-1,3,4-thiadiazol-5-yl) thiomethyl-3-cephem-4-carboxylic acid.

IR(KBr): 3370,2950,1770,1710,1530, 1390 Cm$^{-1}$

NMR(DMSO—d$_6$—D$_2$O): δ1.3-2.4(6H,m, —(CH$_2$)$_3$—),3.59(2H,br,2—CH$_2$),4.10(2H,br,SCH$_2$CO),4.23(2H,br,3—CH$_2$),4.72(1H,t,J=7 Hz, >CH—),5.00(1H,d,J=5 Hz,C$_6$—H),5.57(1H,d,J=5Hz,C$_7$—H),7.90(4H,s,C$_6$H$_4$<)ppm

EXAMPLE 12

To a solution of 240 mg of 1-carboxymethyl-5-mercapto-1H-tetrazole in a mixture of 2 ml of formamide and 4 ml of acetonitrile was added 689 mg of tributylamine salt of 7β-(D-5-carboxyl-5-phthalimidovaleramido)-3-hydroxymethyl-3-cephem-4-carboxylic acid. To the solution were added in sequence 1.0 ml of tetrahydrofuran solution of hydrogen chloride (1 mol/l) and 0.30 ml of trimethyl phosphite. The mixture was stirred at 20 to 25° C. for 2 hours. To the reaction solution was added 20 ml of water, which was concentrated under reduced pressure to distill off acetonitrile. To the concentrate was added 10 ml of tetrahydrofuran, whose pH was adjusted to 2.6 with 4N HCl, followed by separating by addition of 15 ml of methylene chloride. The organic layers were combined and washed with aqueous saline, dried over anhydrous magnesium sulfate, followed by concentration under reduced pressure. The concentrate was poured into ether, then resulting powder was collected by filtration, followed by drying under reduced pressure to obtain 507 mg (yield: 82%) of 3-(1-carboxymethyl-1H-tetrazol-5-yl) thiomethyl-7β-(D-5-carboxy-5-phthalimidovaleramido)-3-cephem-4-carboxylic acid.

IR(KBr): 3300,2940,1770,1710,1530, 1390 cm$^{-1}$

NMR(DMSO—d$_6$—D$_2$O): δ1.3-2.4(6H,m, —(CH$_2$)$_3$—),3.59(2H,br,2—CH$_2$),4.10(2H,br,SCH$_2$CO),4.23(2H,br,3—CH$_2$),4.72(1H,t,J=7 Hz, >CH—),5.00(1H,d,J=5 Hz,C$_6$—H),5.57(1H,d,J=5 Hz,C$_7$—H),7.90(4H,s,C$_6$H$_4$<)ppm

EXAMPLE 13

To a solution of 265 mg of 4,6-dimethyl-2-mercaptopyrimidine hydrochloride in a mixture of 3.5 ml of formamide and 4 ml of acetonitrile were added in sequence 0.31 ml of trimethyl phosphite and 689 mg of tributylamine salt of 7β-(D-5-carboxy-5-phthalimidovaleramido)-3-hydroxymethyl-3-cephem-4-carboxylic acid. The mixture was stirred at 20~25° C. for 1.5 hour, which was subjected to the same treatment as in Example 12 to obtain 573 mg (yield: 91%) of 7β-(D-5-carbyoxy-5-phthalimidovaleramido)-3-(4,6-dimethylpyrimidin-2-yl) thiomethyl-3-cephem-4-carboxylic acid.

IR(KBr): 3260,2950,1775,1715,1580, 1530 cm$^{-1}$

NMR(DMSO—d$_6$): δ1.3-2.3(6H,m,—(CH$_2$)$_3$—), 2.35(6H,s,CH$_3$×2),3.55(2H,ABq,J=18 Hz,2—CH$_2$), 4.15(2H,ABq,J=14 Hz,3—CH$_2$),4.78(1H,br,>CH—), 4.99(1H,d,J=5 Hz,C$_6$—H),5.56(1H,q,J=5×8 Hz, C$_7$—H),6.93(1H,s,Pyrimidine),7.87(4H,s, C$_6$H$_4$<),8.22(1H,d,J=8 Hz,CONH)ppm

EXAMPLE 14

To 1.01 g of 7β-(D-5-carboxy-5-phthalimidovaleramido)-3-hydroxymethyl-3-cephem-4-carboxylic acid were added in sequence 10 ml of tetrahydrofuran, 15 ml of methylene chloride, 0.70 g of 2-ethoxycarbonylmethylthio -5-mercapto-1,3,4-thiadiazole and 0.70 g of triethyl phosphite. The mixture was stirred at 20 to 25° C. for two hours. To the reaction solution was added 10 ml of water, whose pH was adjusted to 2.5 with 4N HCl to allow the mixture to form two layers. To the aqueous layer was added a mixture of 10 ml of tetrahydrofuran and 15 ml of methylene chloride, which was again allowed to form two layers. The organic layers were combined, washed with aqueous saline, dried over anhydrous magnesium sulfate, then concentrated under reduced pressure. To the concentrate was dissolved in a small volume of acetone, and the solution was poured into ether. Precipitating powdery product was collected by filtration and dried under reduced pressure to give 1.12 g (yield: 87%) of 7β-(D-5-carboxy-5-phthalimidovaleramido)-3-(2-ethoxycarbonylmethylthio-1,3,4-thiadiazol-5-yl) thiomethyl-3-cephem-4-carboxylic acid.

IR(KBr): 3300,2950,1775,1530, 1490 cm$^{-1}$

NMR(DMSO—D$_6$): δ1.20(3H,t,CH$_3$),1.4-2.4(6H, m,—(CH$_2$)$_3$—),3.62(2H,br,2—CH$_2$),3.9-4.5(6H,m, COCH$_2$,SCH$_2$CO,3—CH$_2$),4.75(1H,t,J=7 Hz,>CH—), 5.06(1H,d,J=5 Hz,C$_6$—H),5.66(1H,br,C$_7$—H),7.90 (4H,s,C$_6$H$_4$<),8.33(1H,br,CONH)ppm

EXAMPLE 15

To 2.01 g of 7β-(D-5-carboxy-5-phthalimidovaleramido)-3-hydroxymethyl-3-cephem-4-carboxylic acid were added in sequence 4 ml of formamide, 4ml of acetonitrile, 0.95 g of pyridine and 1.5 ml of trimethyl phosphite. The mixture was stirred at 20 to 25° C. for two hours. The reaction solution was cooled, and there were added 40 ml of acetonitrile and 20 ml of ether to cause precipitation of resinous matter. The supernatant was removed by decantation, and the resinous matter was washed twice with 10 ml each portions of acetonitrile. To the resultant material was added 50 ml of fresh acetonitrile and crushed to give homogeneous powder. The powder was collected by filtration, washed with acetonitrile, followed by drying under reduced pressure to give 1.90 g (yield: 84%) of 7β-(D-5-carboxy-5-phthalimidovaleramido)-3-(1-pyridinio)methyl-3-cephem-4-carboxylate.

IR(KBR): 3420,3060,2950,1770,1710, 1390 cm$^{-1}$

NMR(D$_2$O—NaHCO$_3$): δ1.30–2.60(6H,m, —(CH$_2$)$_3$—),3.19(2H,ABq,J=18 Hz,2—CH$_2$),5.90(1H, d,J=5 Hz,C$_6$—H),5.47(2H,ABq,J=13 Hz,3—CH$_2$), 5.61(1H,d,J=5 Hz,C$_7$—H),7.80(4H,s,C$_6$H$_4$<),8.0~9.1(5H,m,Pyridine)ppm

EXAMPLE 16

To 1.51. g of 7β-(D-5-carboxy-5-phthalimidovaleramido)-3-hydroxymethyl-3-cephem-4-carboxylic acid were added in sequence 6 ml of formamide, 1.10 g of isonicotinic acid amide and 6 ml of acetonitrile. To the solution was added, after stirring for 5 minutes, 0.75 ml of trimethyl phosphite. The mixture was stirred at 20 to 25° C. for two hours, to which were added 40 ml of acetonitrile and 20 ml of ether, followed by cooling. Resulting resinous substance was separated and washed with acetonitrile and the product then dissolved in 20 ml of a mixture of water and acetonitrile (1:1,v/v), whose pH was changed to 6.0 with 1N NaOH, followed by concentration under reduced pressure. The concentrate was subjected to an XAD-2 (100 ml) column chromatography, eluting with water and a mixture of water and acetonitrile. Fractions containing the end-product were collected; the pH was adjusted to 6.0and the product was concentrated under reduced pressure, followed by freeze-drying to give sodium 7β-(D-5-carboxylate-5-phthalimidovaleramido)-3-(4-carbamoyl-1-pyridinio)-methyl-3-cephem-4 -carboxylate.

IR(KBr): 3380,1765,1705,1610,1460, 1395 cm$^{-1}$

NMR(D$_2$O): δ1.4–2.6(6H,M,—(CH$_2$)$_3$—),3.26(2H,ABq,J=18 Hz,2—CH$_2$),4.58(1H,t,J=7 Hz, >CH—),5.11(1H,d,J=5 Hz,C$_6$—H),5.53(2H,ABq,J=13 Hz,3—CH$_2$),5.61(1H,d,J=5 Hz,C$_7$—H), 7.78(4H, s,C$_6$H$_4$<),8.42 & 9.16(4H, respectively d,J=7 Hz. Pyridine)ppm

EXAMPLE 17

In 6 ml of formamide was dissolved 1.43 g of 7β-(D-5-benzamido-5-carboxyvaleramido)-3-hydroxymethyl-3-cephem-4-carboxylic acid. To the solution were added in sequence 6 ml of acetonitrile, 0.95 g of pyridine and 1.1 ml of trimethyl phosphite. The reaction was allowed to proceed at 20 to 25° C. for two hours and there was added 60 ml of acetonitrile, followed by cooling. The supernatant was removed by decantation. The residual rubber-like substance was washed with acetonitrile, to which was added 20 ml of a mixture of water and acetonitrile (1:1,v/v), whose pH was adjusted to 6.0 with 1N NaOH. The resultant solution was concentrated under reduced pressure to distill off acetonitrile. The residue was subjected to an Amberlite XAD-2 (100 ml) column chromatography, eluting with water. The fractions containing the end product were combined and freeze-dried to give sodium 7β-(D-5-benzamido-5-carboxylate valeramido)-3-(1-pyridinio)methyl-3-cephem-4-carboxylate.

IR(KBr): 3400,3050,1770,1610,1535, 1485 cm$^{-1}$

NMR(D$_2$O): δ1.50~2.60(6H,m,—(CH$_2$)$_3$—),3.19(2H,ABq,J=18 Hz,2—CH$_2$),4.37(1H,br,>CH—), 5.11(1H,d,J=5 Hz,C$_6$—H),5.23(2H,ABq,J=14 Hz, 3—CH$_2$),5.64(1H,d,J=5 Hz,C$_7$—H),7.30 –9.10(10H, m,C$_6$H$_5$—and Pyridine)ppm

EXAMPLE 18

To 1.73 g of 7β-(D-5-carboxy-5-phenoxycarbonylaminovaleramido)-3-hydroxymethyl-3-cephem-4-carboxylic acid were added 2 ml of formamide, 3 ml of acetonitrile and 0.85 g of isonicotinic acid amide. The mixture was stirred for 5 minutes and there was added 1.1 ml of trimethyl phosphite, followed by stirring at 20 to 25° C. for two hours. To the resultant mixture was added 1 ml of water and it was left standing for 10 minutes. To the reaction solution was added 10 ml of acetonitrile, which was subjected to a silica gel chromatography (using 60 g of silica gel), eluting with a mixture of water and acetonitrile (1:4,v/v). Fractions containing the end product were combined, whose pH was adjusted to 6.5 with 1N NaOH, followed by concentration under educed pressure and freeze-drying to give sodium 7β-(D-5-carboxylate-5-phenoxycarbonylaminovaleramido)-3-(4-carbamoyl-1-pyridinio)methyl-3-cephem-4-carboxylate.

IR(KBr): 3400,1770,1725,1690,1610 cm$^{-1}$

NMR(D$_2$O): δ1.5~2.6(6H,m,—(CH$_2$)$_3$—),3.35(2-H,ABq,J=17 Hz,2—CH$_2$),4.02(1H,br,>CH—),5.17(1H,d,J=5 Hz,C$_6$—H),5.47(2H,ABq, 3—CH$_2$),5.66(1H,d,J=5 Hz,C$_7$—H),7.0–7.6(5H,m,C$_6$H$_5$—),8.32 and 9.11(4H,respectively d.J=8 Hz, pyridine)ppm

EXAMPLE 19

To a solution of 1.22 g of 1-(2-dimethylethyl)-5-mercapto-1H-tetrazole hydrochloride in a mixture of 5 ml of formamide and 4 ml of acetonitrile was added 1.93 g of triethyl phosphite, to which was added a solution of 2.47 g of 7β-(D-5-carboxy-5-phenoxycarbonylaminovaleramido)-3-hydroxymethyl-3-cephem-4-carboxylic acid in a mixture of 5 ml of formamide and 5 ml of acetonitrile. The whole mixture was stirred for 10 minutes and there was added 2 ml of water, followed by standing for 10 minutes. The resultant mixture was concentrated under reduced pressure to distill off acetonitrile. The residual solution was poured into 200 ml of cold water, and precipitates then formed were collected by filtration and washed with water, followed by dissolving in a mixture of acetonitrile and water (4:1,v/v). The solution was subjected to a column chromatography using 50 g of silica gel, eluting with a mixture of acetonitrile and water (4:1,v/v). Fractions containing the end product were combined, concentrated under educed pressure and freeze-drying to give 7β-(D-5-carboxy-5-phenoxycarbonylaminovaleramido)-3-[1-(2-dimethylaminoethyl)-1H-tetrazol-5-yl]-thiomethyl-3-cephem-4-carboxylic acid.

IR(KBr): 3300,1760,1725,1600,1530 cm$^{-1}$

NMR(D$_2$O—NaHCO$_3$): δ1.81(4H,br,—CH$_2$CH$_2$—), 2.40(2H,br,CH$_2$CO),2.63(6H,s,N(CH$_3$)$_2$),3.31(2H, t,J=6 Hz,CH$_2$N),3.56(2H,ABq,J=18 Hz,2—CH$_2$), 4.20(2H,br,3—CH$_2$),5.07(1H,d,J=5 Hz,C$_6$—H), 5.57(1H,d,J=5 Hz,C$_7$—H),7.0–7.6(5H,m,C$_6$H$_5$—) ppm

EXAMPLE 20

To 1.52 g of 7β-(D-5-benzyloxycarbonylamino-5-carboxyvaleramido)-3-hydroxymethyl-3-cephem-4-carboxylic acid was added 0.79 g of 5-mercapto-2-methyl-1,3,4-thiadiazole dissolved in 2 ml of formamide and 8 ml of acetonitrile. To the mixture was added 1.25 g of trimethyl phosphite, which was stirred at 20 to 25° C. for 3 hours. To the reaction solution was added 15 ml of water, which was stirred for 10 minutes, from which acetonitrile was distilled off under reduced pressure. To the residue was added 10 ml of tetrahydrofuran, whose pH was adjusted to 2.6 with 2N HCl, followed by addition of 15 ml methylene chloride to cause the mixture to form two layers. The aqueous layer was subjected to extraction twice more with a mixture of 6 ml of tetra hydrofuran and 9 ml of methylene chloride. The extracts were combined with the organic layer, which was washed with aqueous saline, dried over anhydrous magnesium sulfate, followed by concentration under reduced pressure. The concentrate was dissolved in a small volume of acetone, and the solution was poured into ether. Resulting precipitates were collected by filtration, washed with ether, followed by drying under reduced pressure to give 1.55 g (yield: 83%) of 7β-(D-5-benzyloxycarbonylamino-5-carboxyvaleramido)-3-(2-methyl-1,3,4-thiadiazol-5yl) thiomethyl-3-cephem-4-carboxylic acid.

IR(KBr): 3280,2940,1775,1715,1530 cm$^{-1}$

NMR(DMSO—d$_6$): δ1.65(4H,br,—CH$_2$CH$_2$—),2.17(2H,br,CH$_2$CO),2.68(2H,s,CH$_3$),3.63(2H,br,2—CH$_2$), 4.36(2H,ABq,J=14 Hz,3—(CH$_2$),5.00(3H,br,CH$_2$OCO & C$_6$—H & >CH—),5.62(1H,br,C$_7$—H),7.33(6H,m,C$_6$H$_5$—&CONH),8.80 (1H,br,CONH)ppm

EXAMPLE 21

To 1.34 g of 7β-(D-5-carboxy-5-ethoxycarbonylaminovaleramido)-3-hydroxymethyl-3-cephem-4-carboxylic acid were added in sequence a solution of 0.70 g of 5-mercapto-1-methyl-1H-tetrazole in a mixture of 2 ml of formamide and 8 ml of acetonitrile then 1.25 g of triethyl phosphite, followed by stirring at 20 to 25° C. for 3hours. The reaction solution was subjected to after-treatment in the same manner as in Example 20 to give 1.39 g (yield: 85%) of 7β-(D-5-carboxy-5-ethoxycarbonylaminovaleramido)-3-(1-methyl-1H-tetrazol-5yl) thiomethyl-3-cephem-4-carboxylic acid.

IR(KBr): 3350,2960,1777,1710,1530 cm$^{-1}$

NMR(DMSO—d$_6$): δ1.16(3H,t,J=7 Hz,CH$_2$CH$_3$), 1.61(4H,br,—(CH$_2$)$_2$—),2.18(2H,br,CH$_2$CO),3.67(2H,br,2—CH$_2$),3.93(3H,s,-N—CH$_3$),3.96(2H,q,J=7 Hz,CH$_2$CH$_3$),4.29(2H,br,3—CH$_2$),5.04(1H,d,J=5Hz,-C$_6$—H),5.63(1H,q,J=8×5 Hz,C$_7$—H),7.26(1H,d, J=8 Hz,OCONH),8.76(1H,d,J=8 Hz,CONH)ppm

EXAMPLE 22

In 4 ml of ethyl acetate were dissolved 418 mg of 7β-(D-5-diphenylmethyloxycarbonyl-5-phthalimidovaleramido)-3-hydroxymethyl-3-cephem-4-carboxylic acid diphenyl methyl ester and 116 mg of 5-mercapto-1-methyl-1H-tetrazole. To the solution was added 166 mg of triethyl phosphite, which was stirred at 20 to 25° C. for one hour. To the reaction solution was added 1 ml of n-hexane. The mixture was subjected to a silica gel chromatography, eluting with a mixture of ethyl acetate and n-hexane (4:1,v/v). Fractions containing the end product were combined and concentrated under reduced pressure. To the concentrate was added ether, then precipitating powdery product was collected by filtration, followed by drying under reduced pressure to give diphenylmethyl 7β-(D-5-diphenylmethyloxycarbonyl-5-phthalimidovaleramido)-3-(1-methyl-1H-tetrazol-5-yl) thiomethyl-3-cephem-4-carboxylate.

IR(KBr): 3350,3030,2930,1775,1715 cm$^{-1}$

NMR(DMSO—d$_6$): δ1.30–2.40(6H,m,—(CH$_2$)$_3$—), 3.68(2H,br,2—CH$_2$),3.88(3H,s,N—CH$_3$),4.24(2H,br,3—CH$_2$),4.90–5.20(2H,m,-C$_6$—H > CH—),5.73(1H,q,J=5×8 Hz),6.83 & 6.90(2H,s,—COOCH<×2), 7.10–7.60(20H,m,C$_6$H$_5$—×4),7.91(4H,s,C$_6$H$_4$<), 8.87(1H,d,J=8 Hz,—CONH—)ppm

EXAMPLE 23

To 477 mg of 7β-(D-5-benzamido-5-carboxyvaleramido)-3-hydroxymethyl-3-cephem-4-carboxylic acid and 114 mg of thiourea were added 1 ml of formamide and 3 ml of acetonitrile to make a solution, to which was added 248 mg of trimethyl phosphite. The mixture was stirred at 20 to 25° C. for two hours. To the reaction mixture was added 50 ml of acetonitrile, then precipitating crystals were collected by filtration, washed with acetonitrile and dried to give 466 mg (yield: 87%) of 7β-(D-5-benzamido-5-carboxyvaleramido)-3-carbamimidoylthiomethyl-3-cephem-4-carboxylic acid.

IR(KBr): 3270,3050,1765,1645,1600,1580, 1535 cm$^{-1}$

NMR(D$_2$O—NaHCO$_3$): δ1.5–2.6(6H,m, —(CH$_2$)$_3$—),3.45(2H,s,2—CH$_2$),3.6–4.6(3H,m,3—CH$_2$& >CH—),5.07(1H,d,J=5 Hz,C$_6$—H),5.56(1H,d, J=5 Hz,C$_7$—H),7.4–8.2(5H,m,C$_6$H$_5$—)ppm

EXAMPLE 24

To 582 mg of 7β-[2-(2-thienyl)acetamido]-3-hydroxymethyl-3-cephem-4-carboxylic acid and 174 mg of 5-mercapto-1-methyl-1H-tetrazole was added 12 ml of ethyl acetate to make a solution. To the solution were added in sequence 0.25 ml of trimethyl phosphite and 0.2 ml of ether solution of hydrogen chloride (5mol/l), and the mixture was stirred at 20 to 25° C. for 3hours. To the reaction solution was added 10 ml of water, whose pH was adjusted to 2 with 2N HCl, which was then allowed to form two layers. The aqueous layer was taken, to which was added 10 ml of ethyl acetate. The mixture was allowed to form two layers. The organic layers were combined and washed with 5 ml of aqueous saline, which was dried over anhydrous magnesium sulfate, which was then concentrated under reduced pressure. To the concentrate was added ether, then precipitating powdery product was collected by filtration, washed and dried to give 804 mg (yield: 89%) of 3-(1-methyl-1H-tetrazol-5-yl) thiomethyl-7β-[2-(2-thienyl)acetamido]-3-cephem-4-carboxylic acid.

R(KBr): 1776,1734,1672 cm$^{-1}$

NMR(DMSO—d$_6$): δ3.67(2H,ABq,J=18 Hz,2—CH$_2$), 3.73(2H,s,CH$_2$CO),3.92(3H,s,-N—CH$_3$),4.29(2H, ABq,J=13 Hz,3—CH$_2$),5.05(1H,d,J=5 Hz,C$_6$—H), 5.66(1H,q,J=5×8 Hz,C$_7$—H),6.90 & 7.29(3H,Thienyl 9.10(1H,d,J=8 Hz,CONH)ppm

EXAMPLE 25

Using 450 mg of triethylamine salt of 7β-(2-phenylacetamido)-3-hydroxymethyl-3-cephem-4-carboxylic acid, reaction and after-treatment were conducted in the same manner as in Example 24 to give 385 mg (yield: 86%) of 3-(1-methyl-1H-tetrazol-5-yl)thiomethyl-7β-(2-phenylacetamido)-3-cephem-4-carboxylic acid.

IR(KBr): 1780,1720,1668 cm$^{-1}$

NMR(DMSO—d$_6$—D$_2$O): δ3.56(2H,s,CH$_2$CO),3.69 (2H,br,2—CH$_2$),3.95(3H,s,N—CH$_3$),4.27(2H,br, 3-CH$_2$),5.03(1H,d,J=4.5 Hz,C$_6$—H),5.63(1H,d,J=4.5 Hz,C$_7$—H),7.30(5H,s,C$_6$H$_5$—)ppm

EXAMPLE 26

In a mixture of 4 ml of formamide and 4 ml of acetonitrole was suspended 423 mg of sodium 7β-[2-(2-aminothiazol-4-yl)acetamido]-3-hydroxymethyl-3-cephem-4-carboxylate.dihydrate. To the suspension were added in sequence 315 mg of 1-(2-dimethylaminoethyl)-5-mercapto-1H-tetrazole hydrochloride, 0.45 ml of trimethyl phosphite and 0.20 ml of ether solution of hydrogen chloride (5 mol./l). The mixture was stirred at 20~25° C. for 1.5 hour, and there was added 5 ml of water, followed by concentration under reduced pressure at 20 to 25° C. To the concentrated solution was added 50 ml of water, whose pH was adjusted to 5.8 with 1N NaOH, followed by subjecting the resultant to an Amberlite XAD-2 column chromatography, eluting with a mixture of water and acetone (4:1,v/v). Fractions containing the end product were combined, concentrated under reduced pressure and then freeze-dried to give 7β-[2-(2-aminothiazol-4-yl) acetamido]-3-[1-(2-dimethylaminoethyl)-1H-tetrazol-5-yl]thiomethyl-3-cephem-4-carboxylic acid.

IR(KBr): 3320,1765,1670,1610 cm$^{-1}$

NMR(D$_2$O):

δ3.30(6H,s,—N(CH$_3$)$_2$),3.3~4.0(6H,M,CH$_2$CO & 2—CH$_2$ & —CH$_2$N<),4.21(2H,br,3—CH$_2$), 4.88(2H,t,J=6 Hz,N—CH$_2$),5.10(1H,d,J=5 Hz,C$_6$—H),5.63(1H,d,J=5 Hz,C$_7$—H),6.50(1H,s,-Thiazole)ppm

EXAMPLE 27

In 2 ml of acetonitrile was suspended 103 mg of 7β-[2-(2-aminothiazol-4-yl)-2-(Z)-methoxyiminoacetamido]-3-hydroxymethyl-3-cephem-4 -carboxylic acid. To the suspension were added in sequence 0.10 ml of pyridine, 0.21 ml of triethyl phosphite and 0.2 ml of acetic acid. The mixture was stirred at 20 to 25° C. for 8 hours, followed by concentration under reduced pressure. To the concentrated solution was added 10 ml of tetrahydrofuran, then precipitating powdery product was collected by filtration, followed by concentration under reduced pressure to give 7β-[2-(2-aminothiazol-4-yl)-2-(Z)-methoxyiminoacetamido]-3-(1 -pyridinio)-methyl-3-cephem-4-carboxylate.

IR(KBr): 3350,1771,1660,1620 cm$^{-1}$

NMR(D$_2$O): δ3.18 & 3.65(2H,ABq,J=18 Hz, 2—CH$_2$),3.94(3H,s,OCH$_3$),5.23(1H,d,J=5 Hz,C$_6$—H) ,5.30 & 5.56(2H,ABq,J=15 Hz,3—CH$_2$),5.80(1H, J=5 Hz,C$_7$—H),6.19(1H,s,Thiazole),7.9~8.2 & 8.4–9.0(2H & 3H,m.Pyridine)ppm

EXAMPLE 28

In 2 ml of acetonitrile was suspended 103 mg of 7β-[2(2-aminothiazol-4-yl)-2(Z)-methoxyiminoacetamido]-3-hydroxymethyl-3-cephem-4 -carboxylic acid. To the suspension were added in sequence 0.15 ml of 2,3-cyclopentenopyridine, 0.21 ml of triethyl phosphite and 0.2 ml of acetic acid. The mixture was stirred at 20 to 25° C. for 5.5 hours, and there was added further 0.1 ml of acetic acid. The stirring was conducted for further one hour, which was concentrated under reduced pressure. To the concentrated solution was added 10 ml of tetrahydrofuran, then resulting powdery product was collected by filtration, followed by drying under reduced pressure to give 7β-[2-(2-aminothiazol-4-yl)-2-(Z)-methoxyiminoacetamido]-3-(2,3-cyclopenteno-1 -pyridinio)-methyl-3-cephem-4-carboxylate.

IR(KBr): 3350,1765,1665,1615 cm$^{-1}$

NMR(D$_2$O—NAHCO$_3$):

δ2.0~2.5(2H,m,—CH$_2$CH$_2$CH$_2$—),3.0–3.5(4H,-m,—CH$_2$CH$_2$CH$_2$—),3.16 & 3.46(2 H,ABq,J=18 Hz,2—CH$_2$),3.94(3H,s,OCH$_3$),5.20(1H, d,J=5 Hz,C$_6$—H),5.23 & 5.47(2H,ABq,J=17 Hz, 3—CH$_2$),5.79(1H,d,J=5 Hz,C$_7$—H),6.84(1H,s,-Thiazole), 7.5–7.8 & 8.05–8.55(1H & 2H,m,Pyridine)ppm

EXAMPLE 29

In 4 ml of acetonitrile was suspended 207 mg of 7β-[2-(2-aminothiazol-4-yl)-2-(Z)-methoxyiminoacetamido]-3-hydroxymethyl-3-cephem-4 -carboxylic acid. To the suspension were added in sequence 343 mg of methyl nicotinate, 0.43 ml of triethyl phosphite and 0.4 ml of acetic acid. The mixture was stirred at 20 to 25° C. for 7 hours, and concentrated under reduced pressure. To the concentrated solution was added 10 ml of tetrahyudrofuran, then precipitating powdery product was collected by filtration, followed by drying under reduced pressure to give 218 mg (yield: 82%) of 7β-[2-(2-aminothizol-4-yl)-2-(Z)-methoxyiminoacetamido]-3-(3-methoxycarbonyl-1 -pyridinio)-methyl-3-cephem-4-carboxylate.

IR(KBr): 3375,1770,1735,1665,1620 cm$^{-1}$

NMR(D$_2$O—NaHCO$_3$): δ3.18 & 3.17(2H,ABq,J=18 Hz,2—CH$_2$),3.94(3H,s,NOCH$_3$),4.01(3H,s, COOCH$_3$),5.26(1H,d,J=5 Hz,C$_6$—H),5.34 & 5.69(2H, ABq,J=15 Hz,3—CH$_2$),5.78(1H,d,J=5 Hz,C$_7$—H), 6.81(1H,s,Thiazole),8.0–8.3 & 8.8–9.25(1H & 2H,m,Pyridine),9.55(1H,br,Pyridine)ppm

EXAMPLE 30

In 4 ml of acetonitrile was suspended 207 mg of 7β-[2-(2-aminothiazol-4-yl)-2-(Z)-methoxyiminoacetamido]-3-hydroxymethyl-3-cephem-4 -carboxylic acid. To the suspension were added in sequence 0.25 ml of α-picoline, 0.43 ml of triethyl phosphite and 0.4 ml of acetic acid. The mixture was stirred at 20 to 25° C. for 7 hours, and concentrated under reduced pressure. To the concentrated solution was added 10 ml of tetrahydrofuran, then precipitating powdery product was collected by filtration and dried under reduced pressure to give 7β-[2-(2-aminothiazol-4-yl)-2-(Z)-methoxyiminoacetamido]-3-(2-methyl-1-pyridinio) methyl-3-cephem-4-carboxylate.

IR(KBr): 3350,1770,1660,1620 cm$^{-1}$

NMR(D$_2$O—NaHCO$_3$): δ2.81(3H,s,CH$_3$),3.17 & 3.50(2H,ABq,J=18 Hz,2—CH$_2$),3.95(3H,s,OCH$_3$), 5.22(1H,d,J=5 Hz,C$_6$—H),5.28 & 5.53(2H,ABq,J=17

Hz,3—CH$_2$),5.81(1H,d,J=5 Hz,C$_7$—H),6.90(1H,s,Thiazole),7.6–7.95 & 8.15–8.45 & 8.55–8.75(2H & 1H & 1H,m,Pyridine)ppm

EXAMPLE 31

In 1 ml of formamide were dissolved 207 mg of 7β-[2-(2-aminothiazol-4-yl)-2-(Z)-methoxyiminoacetamido]-3-hydroxymethyl-3-cephem-4 -carboxylic acid and 183 mg of isonicotinic acid amide. To the solution were added in sequence 2 ml of acetonitrile, 0.43 ml of triethyl phosphite and 0.2 ml of acetic acid. The mixture was stirred at 20 to 25° C. for 3 hours, and was concentrated under reduced pressure. The concentrated solution was gradually added dropwise to 50 ml of tetrahydrofuran, then precipitating powdery product was collected by filtration, followed by drying under reduced pressure to give 7β-[2-(2-aminothiazol-4-yl)-2-(Z)-methoxyiminoacetamido]-3-(4-carbamoyl-1-pyridinio) methyl-3-cephem-4-carboxylate.

IR(KBr): 3250,3150,1765,1680,1615 cm$^{-1}$
NMR(D$_2$O—NaHCO$_3$): δ3.21 & 3.70(2H,ABq,J=18 Hz,2—CH$_2$),3.95(3H,s,OCH$_3$),5.26(1H,d,J=5 Hz, C$_6$—H),5.37 & 5.67(2H,ABq,J=15 Hz,3—CH$_2$),5.80(1H,d,J=5 Hz,C$_7$—H),6.87(1H,s,Thiazole),8.31 & 9.08(respectively 2H,d,j=7 Hz,Pyridine)ppm

EXAMPLE 32

In 1 ml of formamide were dissolved 413 mg of 7β-[2-(2-aminothiazol-4-yl)-2-(Z)-methoxyiminoacetamido]-3-hydroxymethyl-3-cephem-4 -carboxylic acid and 0.36 g of imidazo[1,2-a] pyridine. To the solution were added in sequence 2 ml of acetonitrile, 0.86 ml of triethyl phosphite and 0.8 ml of acetic acid. The mixture was stirred at 20 to 25° C. for 14 hours, and concentrated under reduced pressure. The concentrated solution was gradually added dropwise to 70 ml of tetrahydrofuran, then precipitating powdery product was collected by filtration. The powdery product was dissolved in 20 ml of water, which was subjected to an Amberlite XAD-2 column chromatography, eluting with a mixture of water and acetonitrile (9:1,v/v). Fractions containing the end product were combined, concentrated under reduced pressure and freeze-dried to give 7β-[2-(2-aminothiazol-4-yl)-2-(Z)-methoxyiminoacetamido]-3-(imidazo[1,2 -a]pyridinium-1-yl)-methyl-3-cephem-4-carboxylate.

IR(KBr): 3375,1765,1610 cm$^{-1}$
NMR(DMSO—d$_6$): δ2.97 & 3.44(2H,ABq,J=17 Hz, 2—CH$_2$),3.77(3H,s,OCH$_3$),4.97(1H,d,J=5 Hz, C$_6$—H),5.22 & 5.35(2H,ABq,J=14 Hz,3—CH$_2$),5.58(1H,dd,J=5×8 Hz,C$_7$—H),6.65(1H,s,Thiazole). 7.13(2H,br,NH$_2$),7.35–7.6 & 7.8–8.1 & 8.25–8.7 & 8.8–8.95(1H & 1H & 3H & 1H,m,Imidazopyridine), 9.41(1H,d,J=8 Hz,CONH)ppm

EXAMPLE 33

In 1 ml of formamide were dissolved 413 mg of 7β-[2-(2-aminothiazole-4-yl)-2-(Z)-methoxyiminoacetamido]-3-hydroxymethyl-3-cephem-4 -carboxylic acid and 354 mg of imidazo[1.5-a]pyridine. To the solution were added 1 ml of acetonitrile and 0.86 ml of triethyl phosphite, and the mixture was stirred at 20 to 25° C. for 10 hours. The resultant product was treated by the manner of Example 32 to give 7β-[2-(2-aminothiazol-4-yl)-2-(Z)-methoxyiminoacetamido]-3-(imidazo [1,5-a]pyridinium-2-yl)methyl-3-cephem-4-carboxylate.

IR(KBr): 3375,1765,1655,1610 cm$^{-1}$
NMR(DMSO—d$_6$): δ3.13 & 3.45(2H,ABq,J=18 Hz, 2—CH$_2$),3.77(3H,s,OCH$_3$),5.00(1H,d,J=5 Hz,C$_6$—H), 5.04 & 5.51(2H,ABq,J=15 Hz,3—CH$_2$),5.59(1H,dd, J=5×8 Hz,C$_7$—H),6.66(1H,s,-Thiazole),7.13(2H,br,NH$_2$),6.9–7.4 & 7.7–7.9 & 8.4–8.7(2H & 1H & 1H,m) & 8.47 ∝ 10.03(respectively 1H,br. Imidazopyridine),9.37(1H,d,J=8 Hz,CONH)ppm

EXAMPLE 34

In 1 ml of formamide were dissolved 413 mg of 7β-[2-(2-aminothiazol-4-yl)-2-(Z)-methoxyiminoacetamido]-3-hydroxymethyl-3-cephem-4 -carboxylic acid and 357 mg of imidazo[1.2-b]pyridazine. To the solution were added 1 ml of formamide and 0.86 ml of triethyl phosphite. The mixture was stirred at 20 to 25° C. for 5 hours, and treated in the manner of Example 32 to give 7β-[2-(2-aminothiazol-4-yl)-2-(Z)-methoxyiminoacetamido]-3-(imidazo[1,2 -b]-pyridazinium-1-yl)methyl-3-cephem-4-carboxylate.

IR(KBr): 3375,1765,1665,1610 cm$^{-1}$
NMR(DMSO—d$_6$): δ3.30 & 3.48(2H,ABq,J=18 Hz, 2—CH$_2$),3.77(3H,s,OCH$_3$),4.98(1H,d,J=5 Hz, C$_6$—H),5.25 & 5.51(2H,ABq,J=14 Hz,3—CH$_2$),5.59(1H,dd,J=5×8 Hz,C$_7$—H),6.65(1H,s,Thiazole 7.13(2H,br,NH$_2$),7.90(1H,d,J=4×9 Hz) & 8.37(2H,br) & 8.99(1H,d,J=4 Hz) & 9.27(1H,d,J=9 Hz, Imidazopyridazine 8.42(1H,d,J=8 Hz, CONH)ppm

What we claim:

1. In a method for producing a compound of the formula;

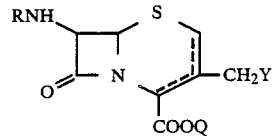

wherein R stands for a hydrogen atom, an acyl group or a protective group other than acyl groups, Q stands for a hydrogen atom or an ester residue, Y stands for the residue of a nucleophilic compound and the dotted line shows the double bond at 2- or 3- position of the cephem ring or a salt thereof, which comprises allowing a compound of the formula

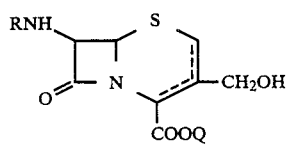

R, Q and the dotted line being of the same meaning as above, or a salt thereof to react with a nucleophilic compound or a salt thereof, the improvement of carrying out the reaction with the use of a compound of the formula

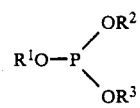

wherein $R^1$, $R^2$, and $R^3$ independently stand for a hydrocarbon group having not more than 8 carbon atoms, or $R^1$ and $R^2$, $R^1$ and $R^3$ or $R^2$ and $R^3$ may be combined to form a polymethylene group that is not a cyclic phosphorus compound.

2. A method according to claim 1, wherein $R^1$, $R^2$ and $R^3$ independently are a $C_{1-8}$ alkyl group.

3. A method according to claim 1, wherein the compound of the formula

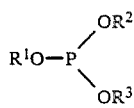

is trimethyl phosphite, triethyl phosphite, triisopropyl phosphite or tri-n-butyl phosphite.

4. A method according to claim 1, wherein the dotted line shows the double bond at 3-position of the cephem ring.

5. A method according to claim 1, wherein the nucleophilic compound is a nitrogen nucleophilic compound.

6. A method according to claim 1, wherein the nucleophilic compound is a sulfur nucleophilic compound.

7. A method according to claim 1, wherein the acyl group represented by R is a group of the formula

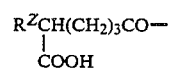

wherein $R^z$ is an amino group which may be protected by an amino-protecting group which are conventionally used for this purpose in the field of synthesizing $\beta$-lactams and peptides.

* * * * *